(12) United States Patent
Rezach et al.

(10) Patent No.: US 11,065,065 B2
(45) Date of Patent: Jul. 20, 2021

(54) SPINAL IMPLANT SYSTEM AND METHODS OF USE

(71) Applicant: Warsaw Orthopedic, Inc., Warsaw, IN (US)

(72) Inventors: William Alan Rezach, Covington, TN (US); Mark C. Dace, Collierville, TN (US); Richard Quinn Brown, Collierville, TN (US); Rodney Ray Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 169 days.

(21) Appl. No.: 16/282,410

(22) Filed: Feb. 22, 2019

(65) Prior Publication Data

US 2020/0268452 A1 Aug. 27, 2020

(51) Int. Cl.
*A61B 17/70* (2006.01)
*A61B 34/20* (2016.01)
*A61B 34/30* (2016.01)
*A61B 90/00* (2016.01)
*A61B 34/10* (2016.01)

(52) U.S. Cl.
CPC .......... *A61B 34/20* (2016.02); *A61B 17/7032* (2013.01); *A61B 17/7082* (2013.01); *A61B 34/30* (2016.02); *A61B 2034/104* (2016.02); *A61B 2034/105* (2016.02); *A61B 2034/2065* (2016.02); *A61B 2034/2072* (2016.02); *A61B 2090/367* (2016.02); *A61B 2090/3762* (2016.02)

(58) Field of Classification Search
CPC ...... A61B 17/7074–7092; A61B 34/30; A61B 34/70; A61B 2034/303; A61B 17/70
See application file for complete search history.

(56) References Cited

U.S. PATENT DOCUMENTS

| | | | |
|---|---|---|---|
| 5,592,939 A | 1/1997 | Martinelli | |
| 5,799,055 A * | 8/1998 | Peshkin | A61B 6/464 378/42 |
| 5,913,820 A | 6/1999 | Bladen et al. | |

(Continued)

FOREIGN PATENT DOCUMENTS

WO 2017221257 12/2017

OTHER PUBLICATIONS

International Search Report and Written Opinion of the International Searching Authority, Korean Intellectual Property Office, PCT/US2019/056260, dated Jan. 30, 2020.

*Primary Examiner* — Eduardo C Robert
*Assistant Examiner* — Michelle C Eckman
(74) *Attorney, Agent, or Firm* — Sorell, Lenna & Schmidt, LLP

(57) ABSTRACT

A method comprises the steps of: imaging a patient anatomy; selecting an implant strategy for at least one bone fastener having a first member; registering the imaging of the patient anatomy with imaging of a surgical driver; engaging the first member with tissue of the patient anatomy via the surgical driver according to the implant strategy; manipulating the patient anatomy; acquiring data points representative of a position of the first member relative to tissue; and retrieving the data points from a computer database for attaching a second member with the first member. Systems, spinal constructs, implants and surgical instruments are disclosed.

20 Claims, 13 Drawing Sheets

(56) References Cited

U.S. PATENT DOCUMENTS

| | | | |
|---|---|---|---|
| 6,021,343 A * | 2/2000 | Foley | A61B 17/16 600/417 |
| 6,725,080 B2 | 4/2004 | Melkent et al. | |
| 6,796,988 B2 | 9/2004 | Melkent et al. | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 8,057,407 B2 | 11/2011 | Martinelli et al. | |
| 8,571,638 B2 | 10/2013 | Shoham | |
| 8,842,893 B2 | 9/2014 | Teichman et al. | |
| 2002/0038118 A1 * | 3/2002 | Shoham | A61B 6/583 606/1 |
| 2003/0181800 A1 * | 9/2003 | Bonutti | A61B 90/39 600/407 |
| 2005/0085714 A1 * | 4/2005 | Foley | A61B 34/20 600/424 |
| 2005/0171553 A1 * | 8/2005 | Schwarz | A61B 34/20 606/96 |
| 2005/0277832 A1 * | 12/2005 | Foley | A61B 34/20 600/426 |
| 2008/0215181 A1 * | 9/2008 | Smith | A61B 90/36 700/245 |
| 2009/0093820 A1 * | 4/2009 | Trieu | A61B 17/701 606/103 |
| 2010/0234725 A1 * | 9/2010 | Geist | A61B 17/7002 600/424 |
| 2010/0249576 A1 * | 9/2010 | Askarinya | A61B 5/6846 600/424 |
| 2011/0152871 A1 * | 6/2011 | Park | A61B 34/30 606/91 |
| 2012/0179214 A1 * | 7/2012 | Geist | A61B 17/7002 606/86 A |
| 2013/0172902 A1 * | 7/2013 | Lightcap | A61B 34/30 606/130 |
| 2013/0345718 A1 * | 12/2013 | Crawford | A61B 17/025 606/130 |
| 2014/0228670 A1 * | 8/2014 | Justis | A61B 17/708 600/409 |
| 2014/0316420 A1 * | 10/2014 | Ballard | A61B 17/7002 606/102 |
| 2015/0032164 A1 * | 1/2015 | Crawford | A61B 34/30 606/279 |
| 2015/0105833 A1 * | 4/2015 | Simpson | A61B 17/8875 606/86 R |
| 2015/0164569 A1 * | 6/2015 | Reitblat | A61B 17/7079 606/279 |
| 2015/0196365 A1 * | 7/2015 | Kostrzewski | A61B 17/17 606/130 |
| 2015/0366624 A1 * | 12/2015 | Kostrzewski | A61B 34/30 606/130 |
| 2016/0128789 A1 | 5/2016 | Kostrzewski et al. | |
| 2016/0151120 A1 * | 6/2016 | Kostrzewski | A61B 90/50 606/130 |
| 2016/0235480 A1 * | 8/2016 | Scholl | A61B 5/0086 |
| 2016/0235481 A1 * | 8/2016 | Dorman | A61B 17/1703 |
| 2017/0140121 A1 * | 5/2017 | Schulhauser | G16H 20/40 |
| 2017/0140127 A1 * | 5/2017 | Schulhauser | G16H 20/30 |
| 2017/0151025 A1 * | 6/2017 | Mewes | A61B 34/30 |
| 2017/0252114 A1 * | 9/2017 | Crawford | A61B 34/30 |
| 2017/0312033 A1 * | 11/2017 | Huang | A61B 17/7077 |
| 2017/0312039 A1 * | 11/2017 | Crawford | A61B 17/8875 |
| 2017/0360515 A1 * | 12/2017 | Kozak | A61B 90/30 |
| 2018/0014890 A1 * | 1/2018 | Stanton | A61B 90/39 |
| 2018/0064497 A1 * | 3/2018 | Hussain | A61B 34/20 |
| 2018/0147018 A1 * | 5/2018 | Crawford | A61B 34/32 |
| 2018/0153592 A1 * | 6/2018 | Larson | A61B 90/50 |
| 2018/0199951 A1 * | 7/2018 | Chappuis | A61B 34/76 |
| 2018/0199999 A1 * | 7/2018 | Syverson | A61B 34/76 |
| 2018/0207794 A1 * | 7/2018 | Sebring | B25J 9/0027 |
| 2018/0256259 A1 * | 9/2018 | Crawford | A61B 6/5217 |
| 2018/0289396 A1 * | 10/2018 | McGahan | A61B 34/37 |
| 2018/0289426 A1 * | 10/2018 | Dace | A61B 17/7076 |
| 2018/0296283 A1 * | 10/2018 | Crawford | G06T 3/0006 |
| 2018/0303522 A1 * | 10/2018 | Wall | A61B 34/20 |
| 2018/0325608 A1 * | 11/2018 | Kang | A61B 34/30 |
| 2018/0344301 A1 * | 12/2018 | Wehrli | A61B 17/00 |
| 2019/0000372 A1 * | 1/2019 | Gullotti | A61B 17/7086 |
| 2019/0021800 A1 * | 1/2019 | Crawford | A61B 34/30 |
| 2019/0029736 A1 * | 1/2019 | Wall | A61B 34/20 |
| 2019/0090966 A1 * | 3/2019 | Kang | A61B 34/10 |
| 2019/0192230 A1 * | 6/2019 | Siemionow | A61B 90/39 |
| 2019/0231435 A1 * | 8/2019 | Zucker | A61B 17/7013 |
| 2019/0231446 A1 * | 8/2019 | Bowling | A61B 34/30 |
| 2019/0231447 A1 * | 8/2019 | Ebbitt | A61F 2/46 |
| 2019/0269469 A1 * | 9/2019 | Bush, Jr. | A61B 34/20 |
| 2019/0350600 A1 * | 11/2019 | Lehman, Jr. | A61B 34/70 |
| 2019/0350657 A1 * | 11/2019 | Tolkowsky | A61B 90/36 |
| 2019/0380794 A1 * | 12/2019 | Al Jewad | A61B 17/7082 |
| 2020/0008884 A1 * | 1/2020 | Lavallee | A61B 34/70 |
| 2020/0038115 A1 * | 2/2020 | Schwamb | A61B 17/2909 |
| 2020/0069376 A1 * | 3/2020 | Garcia | A61B 34/30 |
| 2020/0069377 A1 * | 3/2020 | Finley | A61B 34/20 |
| 2020/0078068 A1 * | 3/2020 | Wall | A61B 17/8886 |
| 2020/0078097 A1 * | 3/2020 | Gregerson | B25J 9/1666 |
| 2020/0085500 A1 * | 3/2020 | Dace | A61B 17/7035 |
| 2020/0121331 A1 * | 4/2020 | Morris | A61B 17/1757 |
| 2020/0121396 A1 * | 4/2020 | Elliott | A61B 17/7082 |
| 2020/0121397 A1 * | 4/2020 | Elliott | A61B 34/20 |
| 2020/0121398 A1 * | 4/2020 | Elliott | A61B 90/39 |
| 2020/0155236 A1 * | 5/2020 | Chi | A61B 34/10 |
| 2020/0197124 A1 * | 6/2020 | Sharifi-Mehr | A61B 17/7032 |
| 2020/0222122 A1 * | 7/2020 | Snyder | A61B 34/30 |
| 2020/0222127 A1 * | 7/2020 | Snyder | A61B 34/20 |
| 2020/0229869 A1 * | 7/2020 | Dorman | A61B 34/25 |
| 2020/0237445 A1 * | 7/2020 | Snyder | A61B 34/30 |
| 2020/0261125 A1 * | 8/2020 | Lorio | A61B 17/704 |
| 2020/0268452 A1 * | 8/2020 | Rezach | A61B 34/30 |
| 2020/0281608 A1 * | 9/2020 | Sharifi-Mehr | A61B 17/1617 |
| 2020/0281664 A1 * | 9/2020 | Stanton | A61B 17/0218 |
| 2020/0282530 A1 * | 9/2020 | Sharifi-Mehr | A61B 17/8886 |

* cited by examiner

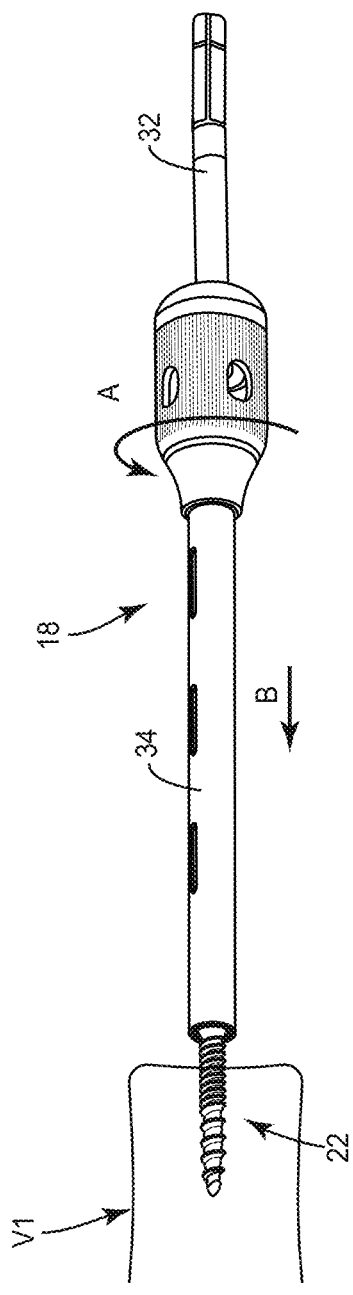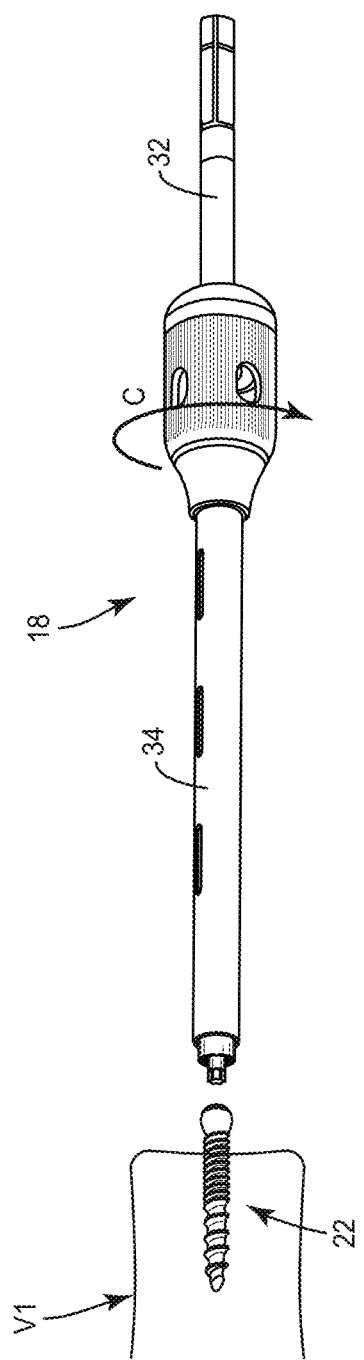

US 11,065,065 B2

SPINAL IMPLANT SYSTEM AND METHODS OF USE

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, interbody devices can be employed with spinal constructs, which include implants such as bone fasteners and vertebral rods to provide stability to a treated region. These implants can redirect stresses away from a damaged or defective region while healing takes place to restore proper alignment and generally support the vertebral members. During surgical treatment, one or more rods and bone fasteners can be delivered to a surgical site. Surgical instruments are employed, for example, to engage the fasteners for attachment to the exterior of two or more vertebral members. This disclosure describes an improvement over these prior technologies.

SUMMARY

In one embodiment, a method for treating a spine is provided. The method comprising the steps of: imaging a patient anatomy; selecting an implant strategy for at least one bone fastener having a first member; registering the imaging of the patient anatomy with imaging of a surgical driver; engaging the first member with tissue of the patient anatomy via the surgical driver according to the implant strategy; manipulating the patient anatomy; acquiring data points representative of a position of the first member relative to tissue; and retrieving the data points from a computer database for attaching a second member with the first member. In some embodiments, systems, spinal constructs, implants and surgical instruments are disclosed.

In one embodiment, the method comprises the steps of: pre-operatively generating a CT scan of a patient anatomy including at least one vertebra; selecting an implant strategy according to the CT scan for at least one bone screw shaft; generating fluoroscopic images of at least a portion of a robot; registering the CT scan with the fluoroscopic images; engaging the bone screw shaft with the vertebra via robotic guidance according to the implant strategy; acquiring a first set of data points representative of a three dimensional position of the at least one bone screw shaft relative to the at least one vertebra; transmitting the first set of data points to a computer database; subsequently, manipulating the patient anatomy; acquiring a second set of data points representative of a three dimensional position of the at least one bone screw shaft relative to the at least one vertebra subsequent to manipulating the patient anatomy; transmitting the second set of data points to the computer database; retrieving the second set of data points from the computer database; aligning an implant receiver with the bone screw shaft according to the second set of data points; and manually engaging the implant receiver with the bone screw shaft to comprise a bone screw.

In one embodiment, the method comprises the steps of: imaging vertebral tissue; selecting an implant strategy for at least one bone screw shaft; registering the imaging of the vertebral tissue with imaging of a robot connected with the vertebral tissue; connecting a surgical driver with the bone screw shaft, the surgical driver including an image guide oriented relative to a sensor to communicate a signal representative of a three dimensional position of the bone screw shaft relative to the vertebral tissue; engaging the bone screw shaft with the vertebral tissue via robotic guidance according to the implant strategy; acquiring a first set of data points representative of the three dimensional position of the at least one bone screw shaft according to the signal; transmitting the first set of data points to a computer database; subsequently, manipulating the vertebral tissue; acquiring a second set of data points representative of a three dimensional position of the bone screw shaft relative to the vertebral tissue subsequent to manipulating the vertebral tissue; transmitting the second set of data points to the computer database; retrieving the second set of data points from the computer database; aligning an implant receiver with the bone screw shaft according to the second set of data points; and manually engaging the implant receiver with the bone screw shaft to comprise a bone screw.

BRIEF DESCRIPTION OF THE DRAWINGS

The present disclosure will become more readily apparent from the specific description accompanied by the following drawings, in which:

FIG. 15 is a perspective view of components of one embodiment of a surgical system in accordance with the principles of the present disclosure disposed with vertebrae;

FIG. 16 is a perspective view of components of one embodiment of a surgical system in accordance with the principles of the present disclosure disposed with vertebrae.

DETAILED DESCRIPTION

Figure 1:
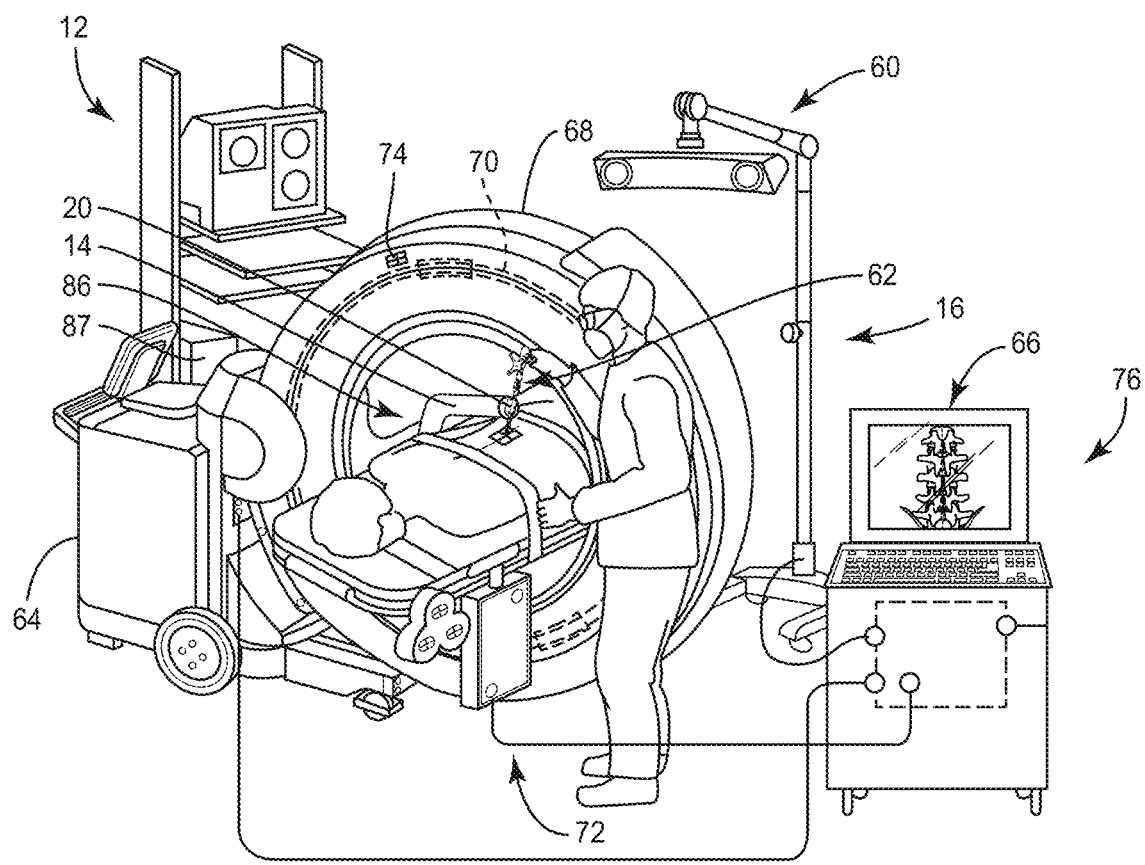
FIG. 1 is a plan view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the present surgical system comprises an image guided, robot assisted spinal implant system. In some embodiments, the present surgical system comprises a robotic guidance system and a selectively coupled bone screw system that allows for operating room assembly of a bone fastener. In some embodiments, the systems and methods of the present disclosure comprise surgical robotic guidance, surgical navigation and medical devices including surgical instruments and implants that are employed with a surgical treatment, as described herein, for example, with a cervical, thoracic, lumbar and/or sacral region of a spine.

In some embodiments, the present surgical system is employed with a method of performing robotically-assisted spinal surgery. In some embodiments, the method includes the step of delivering posterior spinal instrumentation through robotic-assisted trajectory alignment tools. In some embodiments, the present surgical system and method includes surgical robotic guidance having robotic software that performs registration of a patient anatomy to a three dimensional working space of a robot.

In some embodiments, the present surgical system is employed with a method of performing robotically-assisted spinal surgery including the step of generating a pre-operative CT scan that is used to pre-plan locations of pedicle screws for implant in an operating room. In some embodiments, during surgery, the method includes the step of identification of the same patient anatomy as recorded on the pre-operative CT scan. In some embodiments, the patient anatomy is accurately identified and located in the robot's three dimensional coordinate system to proceed with a selected procedure. In some embodiments, registration and placement of the pedicle screws is performed prior to spinal manipulation including decompression, disc preparation and/or interbody insertion, to avoid alteration of a patient's anatomy, for example, vertebral bones.

In some embodiments, the present surgical system is employed with a method of performing robotically-assisted spinal surgery including the step of inserting screws that only have a shank-portion of a screw assembly when using robotic guidance. In some embodiments, after the screw shanks are placed under robotic guidance, decompression, disc preparation and/or interbody insertion can be performed without interference; for example, such interference can occur from screws with implant receivers implanted prior to spinal manipulation, which can interfere with access to a surgical site. In some embodiments, after decompression, disc preparation and/or interbody insertion, implant receivers, for example, modular implant receivers or screw heads may be attached to the screw shanks. In some embodiments, this configuration of the modular screw provides a screw shank having a smaller head/shaft diameter of an unassembled construct, relative to an assembled screw having an implant receiver, which uses robotic guidance for spinal fusion surgery.

In some embodiments, the present surgical system is employed with a method of performing robotically-assisted spinal surgery including the steps of placing a modular head assembly and/or implant receiver on a screw shank, for example, to overcome visibility obstruction and/or visibility challenges associated with screw shank location. In some embodiments, the method includes the steps of placing a pedicle screw shank with vertebral tissue and digitally imaging or digitally acquiring positional data points of a screw trajectory and/or position and location of the placed pedicle screw shank with tissue, and transmitting and storing the data points to a computer database of a surgical robotic guidance system and/or a surgical navigation system, as described herein. In some embodiments, the acquisition of data points step includes surgical robotic guidance having robotic software that performs registration of a position and location of the placed pedicle screw shank with tissue to a three dimensional working space of a robot. In some embodiments, the acquisition of data points step includes performing registration of a position and location of the placed pedicle screw shank with vertebral tissue to a three dimensional working space of a robot, manipulating the vertebral tissue, which may include insertion of interbody implants and/or osteotomies, and performing a registration, subsequent to manipulating the vertebral tissue, of the position and location of the screw shank to the three dimensional working space of the robot. In some embodiments, this configuration allows a robot to reposition and/or align with screw trajectory and/or position of the placed pedicle screw shank to facilitate placement of the modular head assembly and/or implant receiver on a screw shank. In some embodiments, the surgical robotic guidance system can determine and/or the acquired data points can include screw penetration depth with the vertebral tissue and/or a position of a sphere of the screw shank relative to a reference frame, tissue and/or a three dimensional working space of a robot. In some embodiments, the surgical robotic guidance system provides guidance for attaching the modular head assembly and/or implant receiver on a screw shank, and/or determine a desired coupling, as described herein, of the modular head assembly and/or implant receiver on a screw shank. In some embodiments, the surgical navigation system locates and/or aligns the modular head assembly and/or implant receiver with the screw sphere.

In some embodiments, the present surgical system is employed with a method of performing robotically-assisted spinal surgery including the steps of placing a modular head assembly and/or implant receiver on a screw shank using a surgical navigation system and acquiring positional data points of a screw trajectory and/or position of the placed pedicle screw shank with tissue, and transmitting and storing the data points to a computer database of a surgical robotic guidance system and/a surgical navigation system, as described herein. In some embodiments, the modular head assembly and/or implant receiver is guided onto a screw shank. In some embodiments, the surgical navigation system aligns the modular head assembly and/or implant receiver with the screw head based on the relative spatial relationship to screw head. In some embodiments, the present surgical system is employed with percutaneous procedures, for example, which can include visibility obstruction and/or visibility challenges associated with screw shank location and/or screw sphere location and orientation. In some embodiments, the present surgical system includes indicia that the modular head assembly and/or implant receiver is positioned in alignment with the screw sphere location. In some embodiments, computer software of a surgical robotic guidance system and/a surgical navigation system provide confirmation, for example, visual indicia such as a computer display or heads up display showing a colored (for example, green) check mark, colored border or prompt screen, of alignment of the modular head assembly and/or implant receiver with the screw sphere.

In some embodiments, the present surgical system is employed with a method of performing robotically-assisted spinal surgery including the steps of delivering one or more bone fasteners, as described herein, via a surgical robotic guidance system and/or a surgical navigation system, as described herein, implanting the one or more bone fasteners with vertebral tissue, acquiring positional data points of a fastener trajectory and/or position of the implanted bone fastener, and transmitting and storing the data points to a computer database. In some embodiments, the data points include position/location of a connecting feature of the fastener, for example, a screw sphere. In some embodiments, the method includes the step of retrieving fastener location and orientation, for example, screw sphere location and orientation, from the database for each screw and guiding a robot to the sphere for attaching a modular head assembly and/or implant receiver with a screw shank.

In some embodiments, the present surgical system is employed with a method of performing robotically-assisted spinal surgery including the steps of delivering a bone screw via a surgical robotic guidance system and/or a surgical navigation system, as described herein, implanting the bone screw with a vertebral body, acquiring positional data points of a bone screw trajectory and/or position of the implanted bone screw, and transmitting and storing the data points to a computer database of navigation software and/or robotic software. In some embodiments, the data points include screw-receiver geometry, for example, a center location of a screw sphere and may include implant strategy based on receiver size and configuration relative to adjacent vertebral tissue to avoid interference or injury with patient anatomy. In some embodiments, the navigation and/or robotic software retrieves screw-receiver geometry from the database and tracks placement of the receiver relative to screw attachment geometry, for example, a center location of a screw sphere. In some embodiments, this configuration of the present surgical system is employed with minimal access or mini-open surgical procedures.

In some embodiments, the present surgical system is employed with a method that includes the steps of placing a spinal construct having screw-shanks, for example, headless screws that will have modular heads attached thereafter and employed with a robotically-assisted trajectory system. In some embodiments, the present surgical system is employed with a method that includes the steps of registering a robot, placing screw shanks using a robotic trajectory guidance, performing decompression and disc removal, inserting interbody devices with vertebrae, connecting screw heads to the screw shanks, inserting spinal rods with the screw heads and securing the spinal construct with the vertebrae.

In some embodiments, the present surgical system comprises a driver configured for use with a modular screw platform. In some embodiments, the driver is configured for engagement with a screw shank, without a tulip head attached. In some embodiments, the driver includes a collet and a sleeve. In some embodiments, the sleeve is sized to grasp a spherical head of the screw shank. In some embodiments, the surgical system is utilized with a method including the step of disposing a driver in an initial open configuration by translating the sleeve out of engagement with the collet allowing the collet to expand for disposal of the screw shank. In some embodiments, the method includes the step of inserting the screw shank into the collet. In some embodiments, the method includes the step of engaging the screw shank with tissue. In some embodiments, the method includes the step of translating the sleeve out of engagement with the collet to release the screw shank. In some embodiments, the surgical instrument comprises a driver configured to be utilized with multiple design requirements of a modular screw platform. In some embodiments, the surgical instrument includes a driver configured to drive a bone screw shank without a tulip head attached thereto.

In some embodiments, the present surgical system comprises a modular system having a bone fastener including an array of members, such as, for example, receivers that can be selectively coupled to members, such as, for example, bone screw shafts. In some embodiments, the selectively coupled bone fastener is assembled with a force of less than 50 Newtons (N). In some embodiments, the bone fastener comprises manually engaging a screw shaft with a head/receiver of the bone fastener. In some embodiments, the bone fastener comprises manually engaging the screw shaft in a pop-on engagement with the head/receiver of the bone fastener. In some embodiments, a force required to manually engage a screw shaft with a head/receiver of the bone fastener is in a range of 2 to 50 N. In some embodiments, a force required to manually engage a screw shaft with a head/receiver of the bone fastener is in a range of 5 to 10 N. In some embodiments, a screw shaft is manually engaged with a head/receiver of the bone fastener, as described herein, such that removal of the head/receiver from the screw shaft requires a force and/or a pull-out strength of at least 5000 N.

In some embodiments, the bone fastener includes a ring disposed with a receiver connectable with a screw shaft. In some embodiments, the ring is configured to snap onto the screw shaft. In some embodiments, the ring has a minimized thickness and/or height to facilitate snapping the ring onto the screw shaft. In some embodiments, the force required to snap the ring onto the screw shaft is in a range of 2 to 50 N. In some embodiments, the force required to snap the ring onto the screw shaft is in a range of 5 to 10 N.

In some embodiments, the bone fastener is configured for assembly, such as, for example, a practitioner, surgeon and/or medical staff utilizes their hands to apply minimal force for assembly. In some embodiments, the system requires minimal force to attach a receiver and a shaft in-situ thereby reducing a pre-load on the vertebrae, such as, for, example, the pedicle. In some embodiments, the bone fastener includes a receiver having a double ring chamber. In some embodiments, the bone fastener includes an expandable ring. In some embodiments, the bone fastener is configured for assembly with the use of an instrument.

In some embodiments, the bone fastener includes an implant receiver that is rotatable and/or pivotable relative to a screw shaft in a selected range of movement configuration, for example, a multi-axial screw (MAS), a uni-axial screw (UAS) or a fixed angle screw (FAS). In some embodiments, the bone fastener can include one or more multi-axial screws, sagittal angulation screws, pedicle screws, monoaxial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, fixation plates and/or posts.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including surgical robotic guidance, surgical navigation, surgical instruments, spinal constructs, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 can be employed, for example, with a minimally invasive procedure, including percutaneous techniques, mini-open and open surgical techniques to manipulate tissue, deliver and introduce instrumentation and/or components of spinal constructs at a surgical site within a body of a patient, for example, a section of a spine. In some embodiments, one or more of the components of surgical system 10 are configured for engagement with existing spinal constructs, which may include spinal implants such as one or more rods, fasteners, plates and connectors. In some embodiments, the spinal constructs can be attached with vertebrae in a revision surgery to manipulate tissue and/or correct a spinal disorder, as described herein.

Spinal implant system 10, as described herein, includes a surgical robotic guidance system 12 having a robotic arm 14, which is employed with a surgical navigation system 16 and one or a plurality of surgical instruments for manipulating vertebral tissue, and for delivering and introducing components of spinal constructs for engagement with the vertebral tissue. For example, a surgical driver 18 can be employed with an end effector 20 of robotic arm 14 to facilitate implant with robotic arm 14. Driver 18 is guided through end effector 20 for guide-wireless insertion of a spinal implant, such as, for example, a screw shaft 22 of a bone fastener 24.

Screw shaft 22 includes a universal mating element, such as, for example, a head 26 that is universal with a mating element, as described herein, of a receiver 28 to form a selected bone fastener 24 having a selected movement of its components parts and/or movement relative to vertebral tissue. In some embodiments, the selected movement includes rotation and/or pivotal movement of shaft 22 relative to receiver 28 about one or a plurality of axes. In some embodiments, the selected movement includes rotation and/or pivotal movement of shaft 22 relative to receiver 28 through one or a plurality of planes. In some embodiments, shaft 22 is connected to a selected receiver 28 to comprise a MAS, UAS or FAS. In some embodiments, spinal implant system 10 comprises a spinal implant kit, which includes receivers 28 and alternate receivers, such as those described herein. A selected receiver 28 is configured for selection from the kit of receivers 28 such that the selected receiver 28 is connectable with a universal shaft 22. In some embodiments, a selected receiver 28 is configured for selection from the kit of receivers 28 such that receiver 28 is connectable with a compatible shaft 22.

Shaft 22 has a cylindrical cross-sectional configuration and includes an outer surface having an external thread form. In some embodiments, the external thread form may include a single thread or a plurality of discrete threads. In some embodiments, other engaging structures may be located on shaft 22, such as, for example, a nail configuration, barbs, expanding elements, raised elements and/or spikes to facilitate engagement of shaft 22 with tissue. In some embodiments, all or only a portion of shaft 22 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 22 may include one or a plurality of openings. In some embodiments, all or only a portion of the outer surface of shaft 22 may have alternate surface configurations to enhance fixation with tissue, such as, for example, rough, arcuate, undulating, mesh, porous, semi-porous, dimpled and/or textured. In some embodiments, all or only a portion of shaft 22 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of shaft 22 may be cannulated.

Head 26 defines a drive interface, such as, for example, a socket 30. Socket 30 is configured for a mating engagement with driver 18 and defines a hexalobe configuration. Driver 18 includes an inner drive 32 engageable with socket 30 of head 26 and an outer sleeve 34 to dispose driver 18 in a capture orientation of screw shaft 22. In some embodiments, sleeve 34/drive 32 define a cavity configured for disposal of head 26 and sleeve 34 includes an expandable collet to capture shaft 22. In some embodiments, sleeve 34/drive 32 define a cavity configured for disposal of head 26 and sleeve 34 includes a threaded portion (not shown) configured for engagement with a portion of head 26 to pull and/or draw shaft 22 axially into the cavity and into engagement with drive 32 to capture shaft 22.

For example, in use, driver 18 is disposed in an open orientation, such that drive 32 extends from driver 18, as shown in FIG. 15. Drive 32 is aligned with socket 30 and engaged with head 26. Sleeve 34 is rotated relative to drive 32 in a clockwise direction, as shown by arrow A in FIG. 15, such that internal threaded surfaces (not shown) cause sleeve 34 to axially translate, as shown by arrow B in FIG. 15, relative to drive 32 to capture shaft 22 with drive 32. Upon connection and capture of shaft 22, driver 18 is rotated in a clockwise direction, as shown by arrow A in FIG. 15, such that driver 18 is engaged with shaft 22 to manipulate, fasten, drive, torque or insert shaft 22 with tissue, similar to that described herein. To release driver 18 from shaft 22, sleeve 34 is rotated relative to drive 32, in a counter-clockwise direction, as shown by arrow C in FIG. 16, such that sleeve 34 axially translates relative to drive 32 to release head 26 from drive 32. Driver 18 is disengageable from shaft 22.

In some embodiments, upon disposal of shaft 22 with vertebral tissue, as described herein, receiver 28 includes a mating surface 40 configured to interface in a selective mating engagement with head 26. In some embodiments, mating surface 40 includes flats and/or arcuate surfaces to form various bone screw configurations, such as those described herein. Head 26 is slidably engageable with surface 40 and movable relative thereto such that shaft 22 is rotatable along a plurality of axes relative to receiver 28 including rotation about axis X1. As such, universal shaft 22 is connected with a selected receiver 28 from the kit of receivers 28 to form a bone fastener 24.

Receiver 28 defines a groove 42 configured for disposal of a circumferential ring 44, as shown in FIGS. 5-9. Groove 42 includes a circumferential channel 46 having a diameter d1 and a circumferential channel 48 having a diameter d2 that is greater than diameter d1. Channel 48 is adjacent and proximal to channel 46. Channel 48 is separated from channel 46 by a lip 50. In some embodiments, shaft 22 is manually engageable with receiver 28 and/or shaft 22 is coupled with receiver 28 such that ring 44 translates from and into channels 46, 48, and over lip 50, as described herein. Ring 44 is expandable and resilient between a contracted and/or capture orientation, and an expanded orientation, as described herein. Ring 44 facilitates manual engagement of a selected receiver 28 and shaft 22 such that the selected receiver 28 is attached with shaft 22, as described herein.

In some embodiments, manual engagement and/or assembly includes a practitioner, surgeon and/or medical staff grasping receiver 28 and shaft 22 and forcibly assembling the components of bone fastener 24. In some embodiments, manual engagement and/or assembly includes a practitioner, surgeon and/or medical staff grasping receiver 28 and shaft 22 and forcibly snap fitting the components of bone fastener 24 together, as described herein. In some embodiments, manual engagement and/or assembly includes a practitioner, surgeon and/or medical staff grasping receiver 28 and shaft 22 and forcibly pop fitting the components of bone fastener 24 together and/or pop fitting receiver 28 onto shaft 22, as described herein. In some embodiments, a force in a range of 2-50 N is required to manually engage receiver 28 and shaft 22 and forcibly assemble the components of bone fastener 24. For example, a force in a range of 2-50 N is required to snap fit and/or pop fit assemble receiver 28 and shaft 22. In some embodiments, a force in a range of 5-10 N is required to manually engage receiver 28 and shaft 22 and forcibly assemble the components of bone fastener 24. For example, a force in a range of 5-10 N is required to snap fit and/or pop fit assemble receiver 28 and shaft 22. In some embodiments, shaft 22 is manually engaged with receiver 28, as described herein, such that removal of receiver 28 from shaft 22 requires a force and/or a pull-out strength of at least 5000 N. In some embodiments, bone fastener 24 is configured for assembly with the use of an instrument.

Receiver 28 includes a slot 52 configured to receive a flange of a crown 54. Crown 54 is configured for disposal within an implant cavity 56 of receiver 28 and disposal of a spinal rod (not shown). Head 26 is interchangeably engageable with any of the plurality of receivers 28. Head 26 includes a substantially spherical proximal portion configured for moveable disposal with the selected receiver 28 and crown 54. Head 26 includes a plurality of ridges to improve purchase with crown 54. Head 26 has a maximum diameter d3 and applies a force to ring 44 to move ring 44 between a contracted and/or capture orientation and an expanded orientation, as described herein. In some embodiments, head 26 includes universal mating surfaces, such as for example, arcuate portions and/or planar portions configured for disposal with receiver 28 to limit rotation of receiver 28 relative to shaft 22. In some embodiments, receiver 28 may be disposed with shaft 22 in alternate fixation configurations, such as, for example, friction fit, pressure fit, locking protrusion/recess, locking keyway and/or adhesive.

Figure 9:
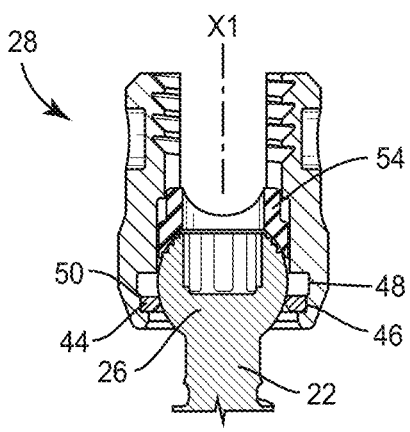
FIG. 9 is a side view of the components shown in FIG. 5.

Receiver 28 extends along and defines an axis X1, as shown in FIG. 9. Receiver 28 includes a pair of spaced apart arms that define implant cavity 56 therebetween configured for disposal of a component of a spinal construct, such as, for example, a spinal rod (not shown). The arms of receiver 28 each extend parallel to axis X1. In some embodiments, the arms may be disposed at alternate orientations, relative to axis X1, such as, for example, transverse, perpendicular and/or other angular orientations such as acute or obtuse, coaxial and/or may be offset or staggered. The arms of receiver 28 each include an arcuate outer surface extending between a pair of side surfaces. At least one of the outer surfaces and the side surfaces of the arms of receiver 28 have at least one recess or cavity therein configured to receive an insertion tool, compression instrument and/or instruments for inserting and tensioning bone fastener 24. In some embodiments, the arms of receiver 28 are connected at proximal and distal ends thereof such that receiver 28 defines a closed spinal rod slot.

Cavity 56 is substantially U-shaped. In some embodiments, all or only a portion of cavity 56 may have alternate cross section configurations, such as, for example, closed, V-shaped, W-shaped, oval, oblong triangular, square, polygonal, irregular, uniform, non-uniform, offset, staggered, and/or tapered. Receiver 28 includes an inner surface having thread forms configured for engagement with a coupling member, such as, for example, a setscrew (not shown), to retain a spinal construct, such as, for example, a spinal rod (not shown) within cavity 56. In some embodiments, receiver 28 may be disposed with the coupling member in alternate fixation configurations, such as, for example, friction fit, pressure fit, locking protrusion/recess, locking keyway and/or adhesive. In some embodiments, receiver 28 may include alternate configurations, such as, for example, closed, open and/or side access.

Figure 2:
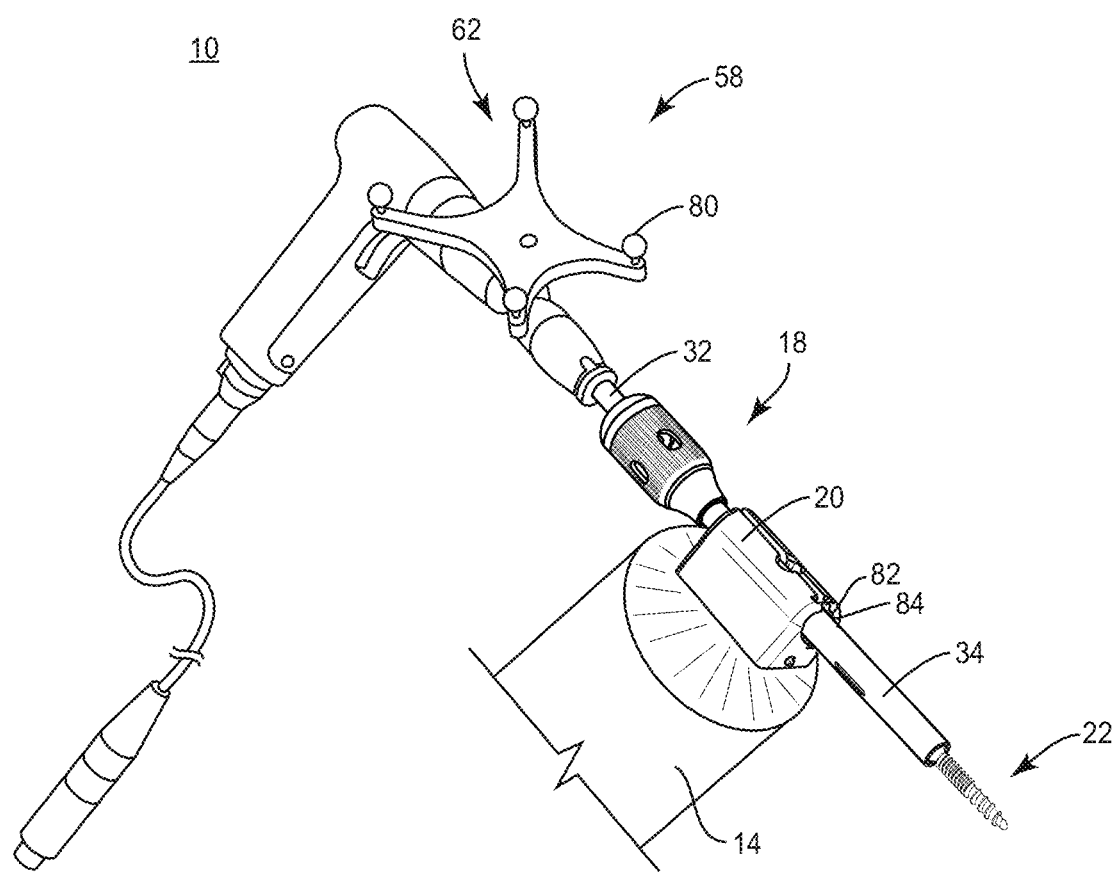
FIG. 2 is a perspective view of components of one embodiment of a surgical system in accordance with the principles of the present disclosure.
Figure 3:
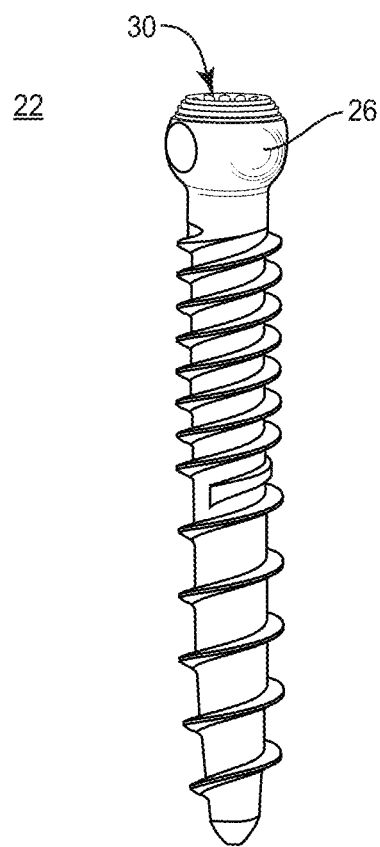
FIG. 3 is a side view of components of one embodiment of a surgical system in accordance with the principles of the present disclosure.
Figure 4:
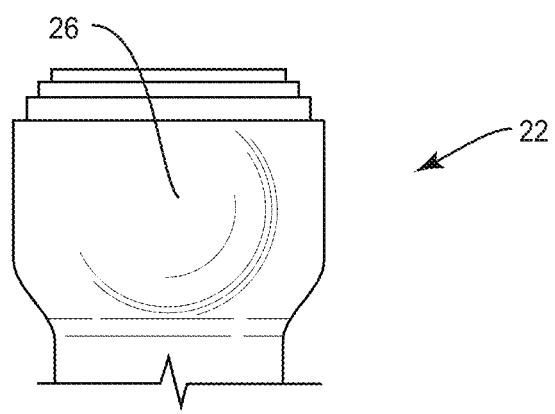
FIG. 4 is a break away view of the components shown in FIG. 3.

In some embodiments, driver 18 includes a navigation component 58, as shown in FIG. 2. Driver 18 is configured for disposal adjacent a surgical site such that navigation component 58 is oriented relative to a sensor array 60, as shown in FIG. 1, to facilitate communication between navigation component 58 and sensor array 60 during a surgical procedure, as described herein. Navigation component 58 is configured to generate a signal representative of a position of screw shaft 22 relative to driver 18 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, navigation component 58 is connected with driver 18 via an integral connection, friction fit, pressure fit, interlocking engagement, mating engagement, dovetail connection, clips, barbs, tongue in groove, threaded, magnetic, key/keyslot and/or drill chuck.

Navigation component 58 includes an emitter array 62. Emitter array 62 is configured for generating a signal to sensor array 60 of surgical navigation system 16. In some embodiments, the signal generated by emitter array 62 represents a position of screw shaft 22 relative to driver 18 and relative to tissue, such as, for example, bone. In some embodiments, the signal generated by emitter array 62 represents a three-dimensional position of screw shaft 22 relative to tissue. In some embodiments, emitter array 62 may include a reflector array configured to reflect a signal from sensor array 60.

In some embodiments, sensor array 60 receives signals from emitter array 62 to provide a three-dimensional spatial position and/or a trajectory of screw shaft 22 relative to driver 18 and/or tissue. Emitter array 62 communicates with a processor of a computer 64 of navigation system 16 to generate data for display of an image on a monitor 66, as described herein. In some embodiments, sensor array 60 receives signals from emitter array 62 to provide a visual representation of a position of screw shaft 22 relative to driver 18 and/or tissue. See, for example, similar surgical navigation components and their use as described in U.S.

Pat. Nos. 6,021,343, 6,725,080, 6,796,988, the entire contents of each of these references being incorporated by reference herein.

Surgical navigation system 16 is configured for acquiring and displaying medical imaging, for example, x-ray images appropriate for a given surgical procedure. In some embodiments, pre-acquired images of a patient are collected. In some embodiments, surgical navigation system 16 can include medical imaging, for example, an O-arm® imaging device 68 sold by Medtronic Navigation, Inc. having a place of business in Louisville, Colo., USA. Imaging device 68 may have a generally annular gantry housing that encloses an image capturing portion 70.

In some embodiments, navigation system 16 comprises image capturing portion 70 that may include an x-ray source or emission portion and an x-ray receiving or image receiving portion located generally or as practically possible 180 degrees from each other and mounted on a rotor (not shown) relative to a track of image capturing portion 70. Image capturing portion 70 can be operable to rotate 360 degrees during image acquisition. Image capturing portion 70 may rotate around a central point or axis, allowing image data of the patient to be acquired from multiple directions or in multiple planes. Surgical navigation system 16 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 16 can include medical imaging, for example, C-arm fluoroscopic imaging systems, which can generate three-dimensional views of a patient. The position of image capturing portion 70 can be precisely known relative to any other portion of an imaging device of navigation system 16. In some embodiments, a precise knowledge of the position of image capturing portion 70 can be used in conjunction with a tracking system 72 to determine the position of image capturing portion 70 and the image data relative to the patient.

Tracking system 72 can include various portions that are associated or included with surgical navigation system 16. In some embodiments, tracking system 72 can also include a plurality of types of tracking systems, such as, for example, an optical tracking system that includes an optical localizer, such as, for example, sensor array 60 and/or an EM tracking system that can include an EM localizer. Various tracking devices can be tracked with tracking system 72 and the information can be used by surgical navigation system 16 to allow for a display of a position of an item, such as, for example, a patient tracking device, an imaging device tracking device 74, and an instrument tracking device, such as, for example, emitter array 62, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to computer 64 where they may be forwarded to a computer 76. Image transfer may be performed over a standard video connection or a digital link including wired and wireless. Computer 76 provides the ability to display, via monitor 66, as well as save, digitally manipulate, or print a hard copy of the received images. In some embodiments, images may also be displayed to the surgeon through a heads-up display.

In some embodiments, surgical navigation system 16 provides for real-time tracking of the position of screw shaft 22 relative to driver 18 and/or tissue can be tracked. Sensor array 60 is located in such a manner to provide a clear line of sight with emitter array 62, as described herein. In some embodiments, fiducial markers 80 of emitter array 62 communicate with sensor array 60 via infrared technology. Sensor array 60 is coupled to computer 64, which may be programmed with software modules that analyze signals transmitted by sensor array 60 to determine the position of each object in a detector space.

Driver 18 is configured for use with end effector 20. End effector 20 includes a surface 82 that defines a channel 84. Channel 84 is configured for passage of the components of bone fastener 24 and disposal of driver 18, and/or spinal construct components and surgical instruments, as described herein. Robotic arm 14 includes position sensors (not shown), similar to those referenced herein, which measure, sample, capture and/or identify positional data points of end effector 20 in three dimensional space for a guide-wireless insertion of components of bone fasteners 24, for example, screw shafts 22 with selected vertebral levels. In some embodiments, surface 82 comprises an axial trajectory guide configured for passage of the components of bone fastener 24 and disposal of driver 18, and/or spinal construct components and surgical instruments, as described herein. In some embodiments, a sleeve, which comprises an axial trajectory guide, is connected with surface 82. In some embodiments, the position sensors of robotic arm 14 are employed in connection with surgical navigation system 16 to measure, sample, capture and/or identify positional data points of end effector 20 in connection with surgical treatment, as described herein. The position sensors are mounted with robotic arm 14 and calibrated to measure positional data points of end effector 20 in three dimensional space, which are communicated to the components of surgical robotic guidance system 12 and/or computer 64. See, for example, the surgical robotic guidance systems and methods described in U.S. Pat. No. 8,571,638, the contents of which being hereby incorporated by reference herein in its entirety.

Surgical robotic guidance system 12 includes a surgical robot 86 including robotic arm 14, which positions one or more surgical instruments, as described herein, with respect to a surgical site and is employed with a method for using robot 86 to assist in surgical procedures. In some embodiments, robot 86 attaches to patient anatomy, for example, bone with a clamp (not shown) or K-wires of robot 86. Robotic arm 14 extends and moves relative to a base of robot 86 to assist in surgical procedures. See, for example, the surgical robot configurations described in U.S. Pat. No. 8,571,638, the contents of which being hereby incorporated by reference herein in its entirety. In some embodiments, robot 86 is not physically connected with the patient anatomy, for example, a navigation system, as described herein, registers the patient anatomy with respect to the location of robot 86, which includes the location of the robot's end effector 20, such that robotic arm 14 extends and moves relative to a base of robot 86 to assist in surgical procedures.

In some embodiments, surgical robotic guidance system 12 includes a control unit 87 that matches data from CT scans and C-arm images to locate surgical robot 86 and allows a surgeon to control surgical robot 86, through the use of a mouse, joystick, touch screen, or the like; and monitor 66. In some embodiments, control unit 87 may include a central processing unit (CPU) and user interface communicating with monitor 66 and surgical robot 86. Surgical robot 86 aligns end effector 20 and drive 18 for alignment with a surgical site requiring a surgical procedure percutaneously, mini-open or in open procedures.

Figure 10A:
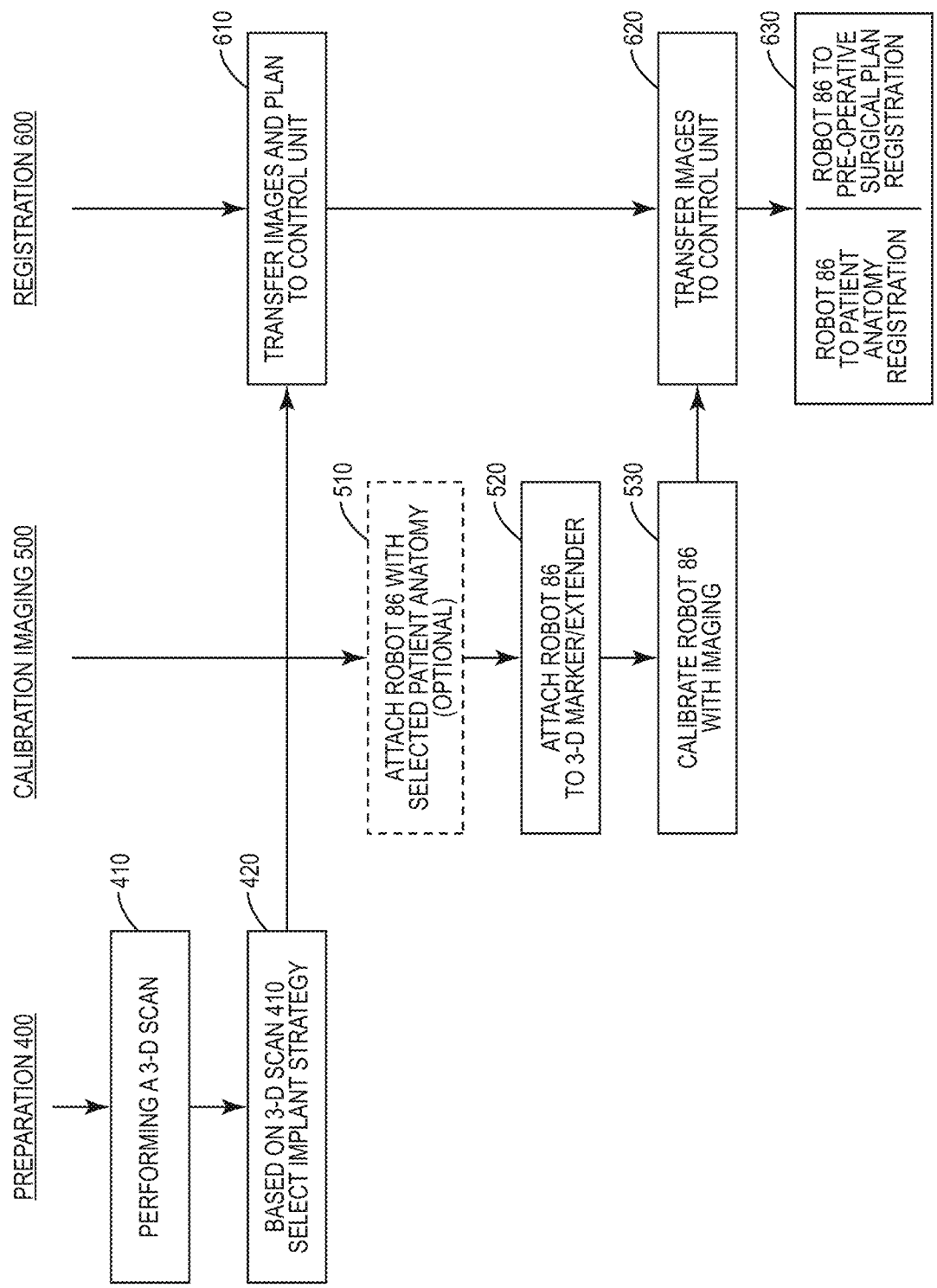
FIGS. 10A and 10B are flow diagrams illustrating representative steps of embodiments of a method and a surgical system in accordance with the principles of the present disclosure.

In one embodiment, as shown in FIGS. 10A-12, spinal implant system 10, similar to the systems and methods described herein, is employed in connection with one or more surgical procedures, as described herein. Initially, spinal implant system 10 is employed with a method for treating a spine that includes a preparation and/or a pre-operative step 400, as shown in FIG. 10A. Preparation step 400 includes imaging a patient anatomy, for example, pre-operatively generating three dimensional images of the patient anatomy. In some embodiments, preparation step 400 includes performing a three-dimensional scan in an imaging step 410, for example, a CT scan or MRI scan, of the patient anatomy, for example, the spine. In some embodiments, preparation step 400 may include verification of surgical instruments, draping and/or camera positioning. In some embodiments, the preparation step includes utilizing O-Arm® imaging device 68 in the operating room to obtain the three-dimensional images of the patient anatomy intra-operatively and/or prior to surgery 700.

Figure 11:
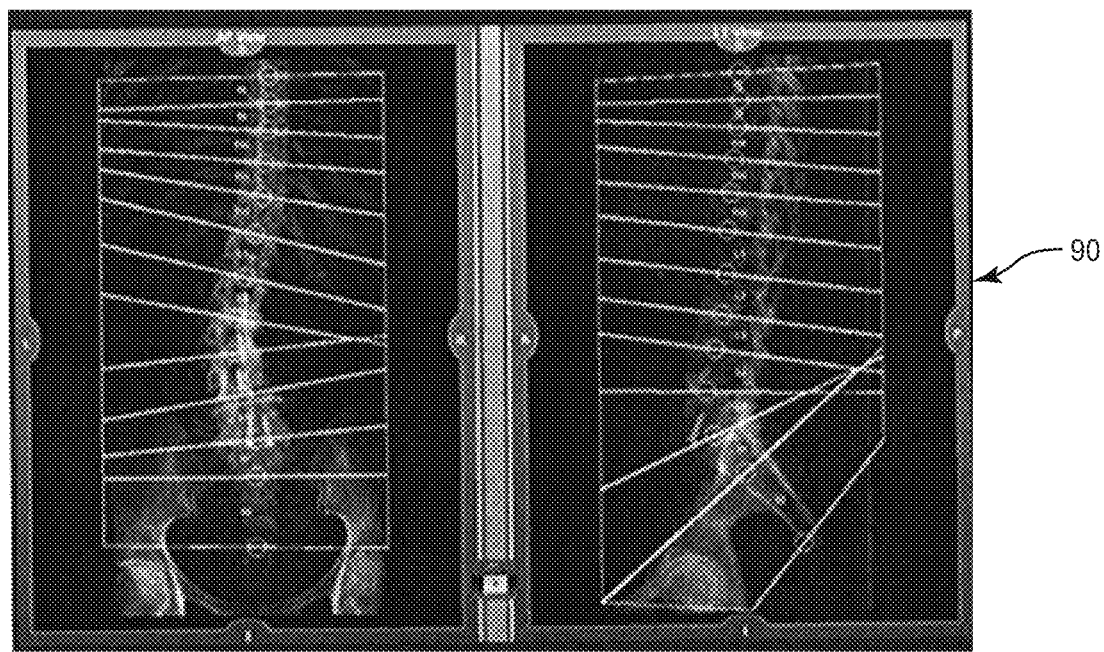
FIG. 11 is a graphical representation of components of one embodiment of a surgical system in accordance with the principles of the present disclosure.
Figure 12:
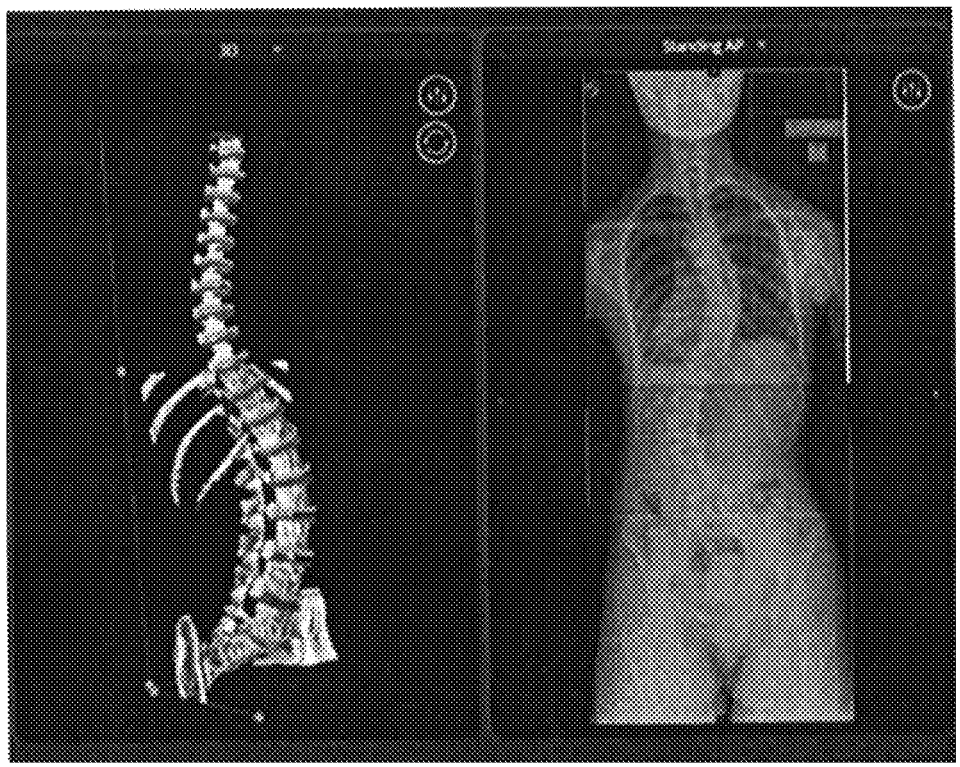
FIG. 12 is a graphical representation of components of one embodiment of a surgical system in accordance with the principles of the present disclosure.

A surgeon reviews three-dimensional scan 410 and formulates and selects an implant strategy 420 for the components of a spinal construct with the patient anatomy according to three-dimensional scan 410. In some embodiments, implant strategy 420 includes preparing a pre-operative surgical plan based on three-dimensional scan 410. In some embodiments, implant strategy 420 includes selecting an insertion path, for example, screw trajectory of screw shaft 22 and positioning of screw shaft 22 with the vertebral tissue. In some embodiments, implant strategy 420 includes selecting a plurality of screw trajectories for positioning a plurality of screw shafts 22 with vertebrae of the patient anatomy. In some embodiments, implant strategy 420 employs pre-operative analytics software including anatomy recognition and vertebral segmentation algorithms for surgical visualization based on a patient's images, for example as shown in FIGS. 11 and 12, which facilitates formulating implant strategy 420 including implant and trajectory placement planning. In some embodiments, implant strategy 420 may be created pre-operatively or intra-operatively. Implant strategy 420 includes surgical parameters of trajectory and positioning of one or more implants, which are communicated to surgical robotic guidance system 12 to direct robot 86 to a location where a surgical procedure is to be performed to assist in surgical procedures.

In some embodiments, a calibration imaging step 500 includes making an incision in the patient at a site where a connecting member, such as, for example, a clamp or a pin (not shown) of robot 86 is attached to a selected portion of the patient anatomy, such as, for example, vertebra in a step 510. In some embodiments, the clamp is attached with a pelvis, sacrum or ilium of the patient. The clamp is configured to secure robot 86 with the patient. The clamp stabilizes robot 86 with the patient to resist and/or prevent relative movement. In some embodiments, the clamp includes an emitter or reflector array to communicate a signal to sensor array 60. In some embodiments, calibration imaging step 500 includes robot 86 not being physically connected with the patient anatomy. For example, surgical navigation system 16 registers the patient anatomy, as described herein, relative to the location of robot 86, which includes the location of the robot's end effector 20, such that robotic arm 14 extends and moves relative to a base of robot 86 to assist in surgical procedures. The patient anatomy and robot 86 may each have reference markers, similar to those described herein, which are visible by surgical navigation system 16. This, in combination with imaging of the patient anatomy, as described herein and stored with surgical robotic guidance system 12 and/or surgical navigation system 16, enables registering the patient's anatomy with respect to location of robot 86.

Figure 10B:
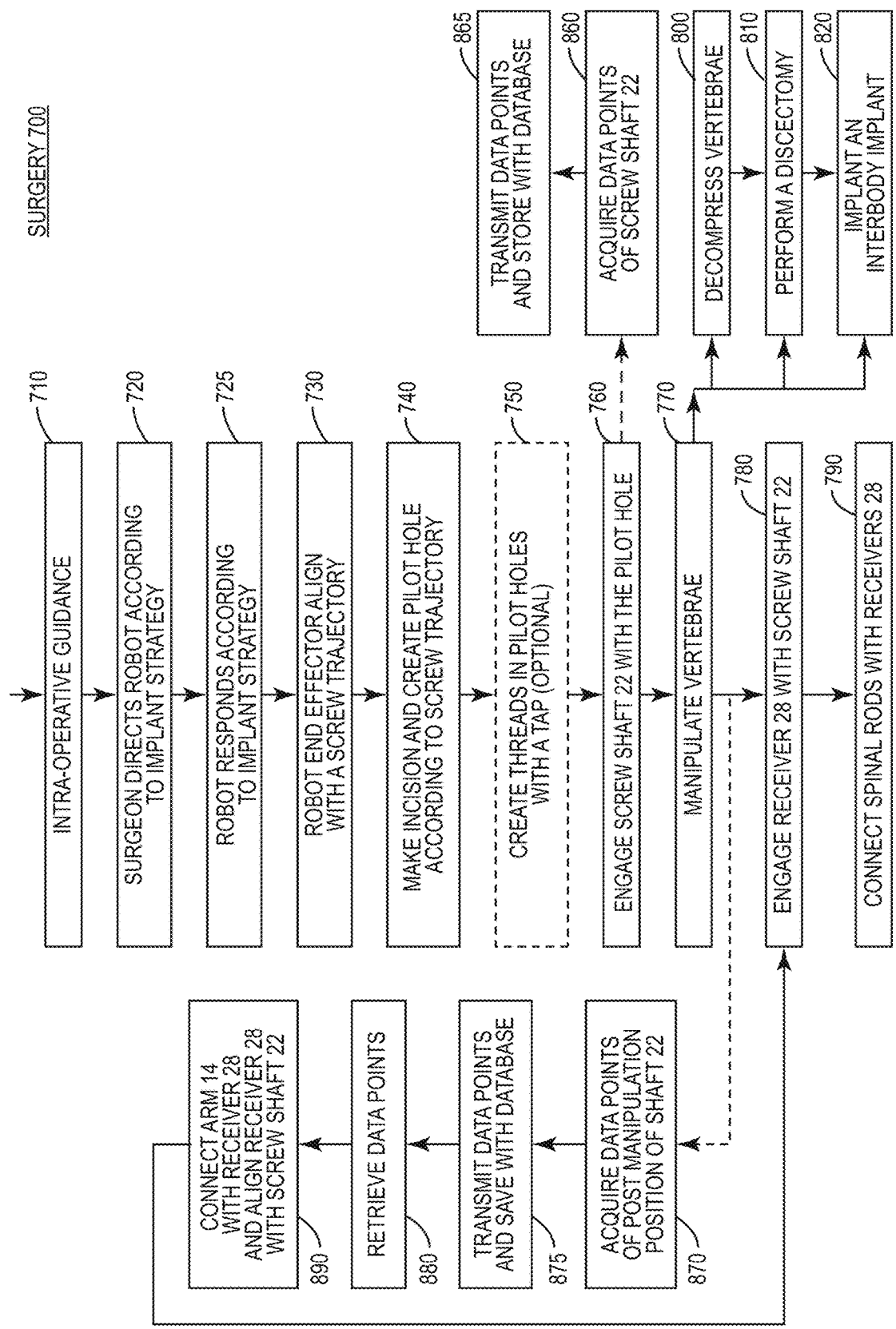
Figure 10C:
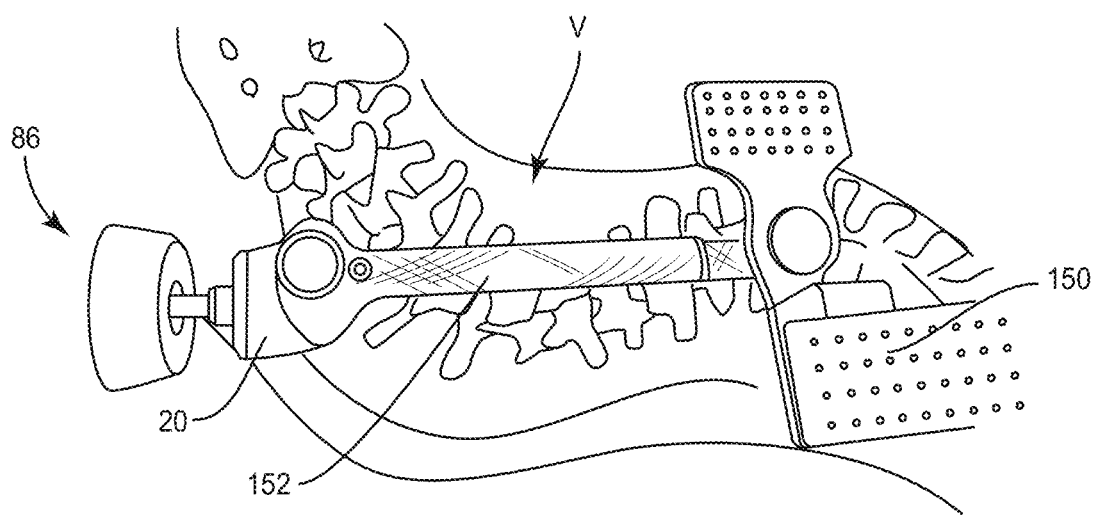
FIG. 10C is a plan view of components of one embodiment of a surgical system in accordance with the principles of the present disclosure.

A calibration step 520 includes attaching a 3D marker 150 and a target extender 152 with end effector 20 of robot 86, as shown in FIG. 10C. In some embodiments, robot 86 includes marker 150 and/or extender 152. Robot 86 is calibrated in a step 530 by obtaining imaging of the selected vertebra of the patient on the table in the operating room. In some embodiments, the images include taking C-arm images of the patient anatomy and these images are calibrated such that a three-dimensional image of the selected vertebra is generated. In some embodiments, fluoroscopic images are taken from different angles, such as, 0, 45, and 90 degrees. In some embodiments, multiple C-arm images are taken.

During a registration process 600, the three-dimensional scans 410 from preparation step 400 are transferred in a step 610 to control unit 87. The C-arm images from step 530 are transferred in a step 620 to control unit 87. A pseudo three-dimensional image of the selected vertebra is generated in a robot 86 to patient anatomy registration 630. In some embodiments, registration 630 includes robot 86 not being physically connected with the patient anatomy, as described herein. The three-dimensional scan 410 is matched with the multiple C-arm images in a robot 86 to the pre-operative surgical plan registration 630. See, for example, the registration systems and methods, as described in U.S. Pat. No. 8,571,638, the contents of which being hereby incorporated by reference herein in its entirety. Robot 86 is located adjacent to the selected vertebra in a three-dimensional image and can be manipulated by the surgeon according to implant strategy 420 for insertion of surgical tools, medical devices, or implants with a surgical site. Robot 86 can be controlled from control unit 87 and/or computers 64, 76.

In some embodiments, registration is accomplished by taking windows 90 of images of a surgical site, as shown in FIGS. 11 and 12. In some embodiments, windows 90 are selected that specifically relate to the known location of robot 86. Windows 90 are selected from the C-arm (fluoroscopic) image data. In some embodiments, the same windows are chosen from both the pseudo three-dimensional hybrid C-arm image and from the CT image (3D image).

During a surgery 700, as shown in FIG. 10B, surgical robotic guidance system 12 includes intra-operative guidance 710 such that a surgeon directs robot 86, in a step 720, to guide surgical instruments, as described herein, and implants at a trajectory and position according to implant strategy 420. Robot 86 responds, in a step 725, and moves end effector 20, which includes an axial trajectory guide, for example, channel 84 and/or a sleeve disposed with surface 82, into position, such that a spinal construct component and/or surgical instrument disposed with end effector 20 can be aligned with a location according to implant strategy 420. In some embodiments, the surgeon can insert a spinal construct component and/or surgical instrument with end effector 20 and visually verify positioning of the spinal construct component and/or surgical instrument from control unit 87 and/or monitor 66. In some embodiments, a surgeon can manipulate robot 86 by use of a joystick, mouse and/or touch screen.

The components of spinal implant system 10 can be employed with surgery 700 for treatment of an applicable condition or injury of an affected section of a spinal column and adjacent areas within a body, such as, for example, vertebrae V. To treat a selected section of vertebrae V, a medical practitioner obtains access to a surgical site including vertebrae V in any appropriate manner, such as through incision and retraction of tissues. In some embodiments, the components of spinal implant system 10 can be used in any existing surgical method or technique including open surgery, mini-open surgery, minimally invasive surgery and percutaneous surgical implantation, whereby vertebrae V are accessed through a mini-incision, or sleeve that provides a protected passageway to the area. Once access to the surgical site is obtained, the particular surgical procedure can be performed for treating the spine disorder.

Channel 84 of end effector 20 provides an axial guide for spinal construct components and/or surgical instruments according to implant strategy 420 and/or a surgical pathway for delivery of components of spinal implant system 10, which may include, such as, for example, drivers, extenders, reducers, spreaders, distractors, blades, clamps, forceps, elevators and drills, which may be alternately sized and dimensioned, and arranged as a kit. In some embodiments, the surgeon disposes a sleeve (not shown) with end effector 20, which provides an axial guide.

Figure 13:
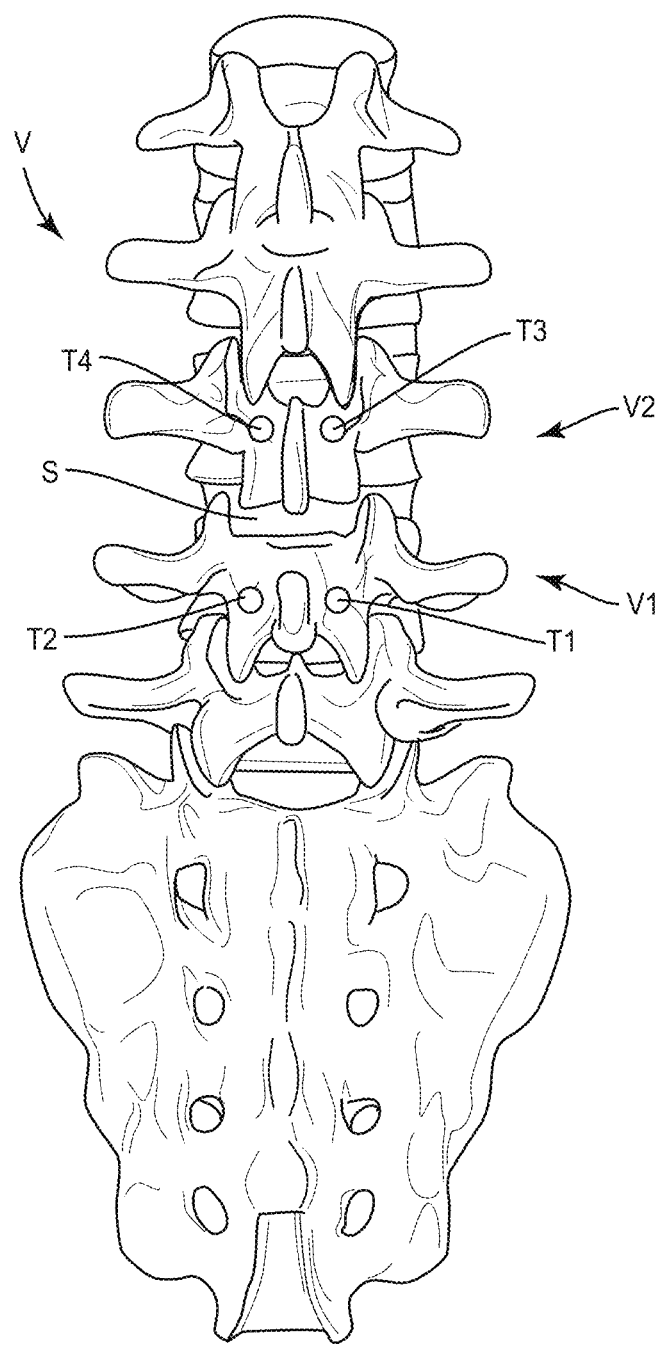
FIG. 13 is a plan view of one embodiment of an implant strategy with vertebrae in accordance with the principles of the present disclosure.

For example, implant strategy 420 includes a screw trajectory T1 of an insertion path and positioning of a screw shaft 22 with a lateral side of a vertebra V1, as shown in FIG. 13. Screw trajectory T1 includes an axial or linear pathway for delivering spinal construct components and/or surgical instruments to a selected location of the lateral side of vertebra V1, according to implant strategy 420.

During surgery 700, in a step 730, the surgeon moves arm 14 such that channel 84 is aligned with screw trajectory T1. In some embodiments, channel 84 and/or a sleeve, cannula and/or dilator disposed with channel 84 defines a surgical pathway along screw trajectory T1 to vertebra V1. In some embodiments, surface 82 of end effector 20 may be connected, attached or monolithically formed with a sleeve, cannula and/or dilator to define the surgical pathway along screw trajectory T1 to vertebra V1.

In a step 740, with channel 84 oriented along screw trajectory T1, the surgeon positions a cutting instrument (not shown) within the surgical pathway of channel 84. The cutting instrument is translated by the surgeon through channel 84 in alignment with screw trajectory T1 and creates an incision in the surgical pathway through tissue to vertebra V1. The surgeon removes the cutting instrument from channel 84. Alignment of channel 84 with screw trajectory T1 is maintained and the surgeon positions a drill (not shown) within the surgical pathway of channel 84. The drill is translated by the surgeon through the surgical pathway of channel 84 in alignment with screw trajectory T1. In some embodiments, a cannula or a drill guide is disposed with channel 84 to protect tissue and facilitate insertion and guidance of the drill. The drill is actuated to create a pilot hole in vertebra V1 along screw trajectory T1. The drill is removed from the surgical pathway of channel 84.

Figure 14:
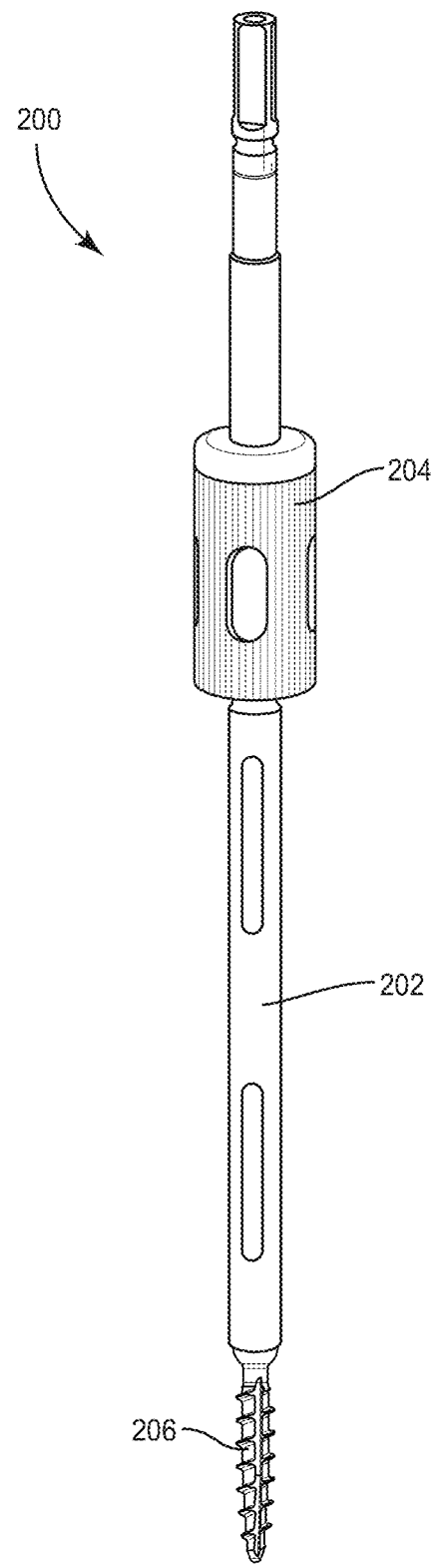
FIG. 14 is a perspective view of components of one embodiment of a surgical system in accordance with the principles of the present disclosure.

In some embodiments, in a step 750, alignment of channel 84 with screw trajectory T1 is maintained and the surgeon positions a tap instrument 200 within the surgical pathway of channel 84. Tap instrument 200, as shown in FIG. 14, forms threads in vertebral tissue about the pilot hole to facilitate fixation and positioning of screw shaft 22 with vertebra V1 along screw trajectory T1 and according to implant strategy 420. Tap instrument 200 includes a shaft 202 and a handle 204. In some embodiments, tap 200 is configured for connection with an actuator, such as, for example, a motorized actuator, such as, for example, a powered drill (not shown). Tap instrument 200 includes a cavity configured for insertion and internal connection of a threaded tap 206 configured to form an internal or female thread in tissue such that screw shaft 22 can be threaded into the internal thread formed by tap instrument 200. Tap instrument 200 is actuated to create threads in vertebral tissue about the pilot hole and removed from the surgical pathway of channel 84.

In a surgical step 760, alignment of channel 84 with screw trajectory T1 is maintained and prior to manipulation of vertebrae V, for example, decompression, disc preparation and/or interbody insertion, screw shafts 22 are engaged with vertebrae V. For example, screw shaft 22 is connected with driver 18, as described herein. The surgeon positions driver 18 with screw shaft 22 extending therefrom within the surgical pathway of channel 84. Driver 18 is translated by the surgeon through the surgical pathway of channel 84 in alignment with screw trajectory T1. Screw shaft 22 engages vertebra V1 and driver 18 is manipulated to drive, torque, insert or otherwise connect screw shaft 22 with the pilot hole of vertebra V1 along screw trajectory T1 and according to implant strategy 420, as shown in FIG. 15 Driver 18 is disengaged from screw shaft 22, as described herein and shown in FIG. 16. Driver 18 is removed from the surgical pathway of channel 84.

In one embodiment, as shown in FIG. 10B, during surgery 700, screw shaft 22 is fixed with vertebra V1 along screw trajectory T1 according to implant strategy 420, as described with regard to surgical step 760, and in a surgical step 860, driver 18 and/or the position sensors of robot 86 generate a signal, similar to that described herein, representative of a three-dimensional position of screw shaft 22 relative to vertebra V1. For example, navigation component 58 of driver 18 generates a signal representative of a position of screw shaft 22 relative to driver 18 and/or vertebra V1, and/or robotic arm 14 includes position sensors, which identify positional data points of end effector 20 to facilitate acquisition of data points of the three-dimensional position of screw shaft 22 relative to vertebra V1. In one example, the acquired data points include position, orientation and/or location of a connecting feature of screw shaft 22, such as head 26. In one example, the acquired data points include screw-receiver geometry such as a center location of head 26 and may include implant strategy 420 based on receiver 28 size and configuration relative to vertebrae V to avoid interference or injury with patient anatomy.

In a step 865, navigation component 58 transmits the signal and communicates with a processor of computer 64 of navigation system 16, similar to that described herein, which digitally acquires the data points of screw trajectory T1 and/or position, orientation and/or location of screw shaft 22 fixed with vertebra V1 to generate data for display of an image of screw shaft 22 fixed with vertebra V1 on a monitor 66, as described herein. See, for example, similar surgical navigation components and their use as described in U.S. Pat. Nos. 6,021,343, 6,725,080, 6,796,988, the entire contents of each of these references being incorporated by reference herein. In some embodiments, surgical robotic guidance system 12 and/or surgical navigation system 16 digitally acquire data points of screw trajectory T1 and/or position, orientation and/or location of screw shaft 22 fixed with vertebra V1 from medical imaging, as described herein, which is transmitted to a corresponding computer database for storage. In some embodiments, surgical robotic guidance system 12 and/or surgical navigation system 16 determines and/or the acquired data points can include position, orientation and/or location of screw shaft 22 relative to vertebra V1, for example, screw shaft 22 penetration depth with vertebra V1 for attaching receiver 28 with screw shaft 22.

For example, in step 865, the acquired data points of screw shaft 22 relative to vertebra V1 are transmitted to computer 64 where they may be forwarded to a computer 76, and may be saved with a database for retrieval during surgery, similar to that described with regard to surgical step 880. In some embodiments, the acquired data points of screw shaft 22 relative to vertebra V1 can be displayed via monitor 66, and digitally manipulated, or printed. In some embodiments, images may also be displayed to the surgeon through a heads-up display. In some embodiments, surgical navigation system 16 provides for real-time tracking, as described herein, of the position of screw shaft 22 relative to vertebra V1. In some embodiments, the position sensors are mounted with robotic arm 14 and calibrated to measure positional data points of end effector 20 in three dimensional space, which are communicated to the components of surgical robotic guidance system 12 and/or computer 64. See, for example, the surgical robotic guidance systems and methods described in U.S. Pat. No. 8,571,638, the contents of which being hereby incorporated by reference herein in its entirety.

In some embodiments, surgical navigation system 16 registers the acquired data points of screw shaft 22 relative to vertebra V1, as described herein, relative to patient anatomy and/or a three dimensional working space of robot 86, similar to that described herein, and may include a reference marker visible by surgical navigation system 16. This configuration of spinal implant system 10, in combination with imaging of the patient anatomy, is saved with a database of surgical robotic guidance system 12 and/surgical navigation system 16 and enables registering the acquired data points of screw shaft 22 relative to vertebra V1 and/or three dimensional working space of robot 86. In some embodiments, surgical step 860 includes a calibration step and/or surgical plan registration for attaching receiver 28 with screw shaft 22 employing medical imaging, similar to that described herein.

In some embodiments, implant strategy 420 includes a screw trajectory T2 of an insertion path and positioning of a screw shaft 22 with a contra-lateral side of vertebra V1, as shown in FIG. 13, similar to screw trajectory T1 described herein. Arm 14 is moved to align channel 84 with screw trajectory T2 and define a surgical pathway along screw trajectory T2 to vertebra V1, similar to that described with regard to step 730. An incision and pilot hole are created in vertebra V1 along screw trajectory T2, similar to that described with regard to step 740. In some embodiments, a tap instrument may be used to form threads in vertebral tissue about the pilot hole of vertebra V1 along screw trajectory T2, similar to that described with regard to step 750. Driver 18 is connected with screw shaft 22, which engages vertebra V1 along screw trajectory T2 and according to implant strategy 420, similar to that described with regard to step 760. In some embodiments, surgical robotic guidance system 12 and/or surgical navigation system 16 digitally acquire data points of screw trajectory T2 and/or position, orientation and/or location of screw shaft 22 fixed with vertebra V1 for attaching receiver 28 with screw shaft 22, similar to that described with regard to surgical step 860.

In some embodiments, implant strategy 420 includes screw trajectories T3, T4 of insertion paths and positioning of screw shafts 22 with a lateral and contra-lateral side, respectively, of vertebra V2, as shown in FIG. 13, similar to screw trajectories T1, T2 described herein. Arm 14 is moved to align channel 84 and define respective surgical pathways along screw trajectories T3, T4 to vertebra V2, similar to that described with regard to step 730. Incisions and pilot holes are created in vertebra V2 along screw trajectories T3, T4, similar to that described with regard to step 740. In some embodiments, a tap instrument may be used to form threads in vertebral tissue about the pilot holes of vertebra V2 along screw trajectories T3, T4, similar to that described with regard to step 750. Driver 18 is connected with screw shafts 22, which engage vertebra V2 along screw trajectories T3, T4, respectively, and according to implant strategy 420, similar to that described with regard to step 760. In some embodiments, surgical robotic guidance system 12 and/or surgical navigation system 16 digitally acquire data points of screw trajectories T3, T4 and/or position, orientation and/or location of screw shafts 22 fixed with vertebra V2 for attaching receivers 28 with screw shafts 22, similar to that described with regard to surgical step 860. In some embodiments, implant strategy 420 may include one or a plurality of screw insertion paths and/or trajectories.

With one or more screw shafts 22 engaged with vertebrae V, as described during surgery 700, vertebrae V is subsequently manipulated in a step 770 for selected treatment in connection with a surgical procedure, as described herein. In some embodiments, robot 86 and/or arm 14 can be moved out alignment with the screw trajectories, or withdrawn from the surgical site. For example, in a step 800, a decompression instrument, such as, for example, a distractor (not shown) is attached with heads 26 of screw shafts 22. The distractor manipulates vertebrae V to rotate, for example, vertebra V2 relative to vertebra V1 to decompress intervertebral space S between vertebrae V, relieve disc pressure, realign one or more vertebra and/or reduce compression on the spinal cord and adjacent nerves.

In some embodiments, manipulation step 770 can include a step 810, which includes discectomy performed, for example, between vertebra V1 and vertebra V2 for selected treatment in connection with a surgical procedure, as described herein. A discectomy instrument, such as, for example, a cutter (not shown) is employed to engage tissue between vertebra V1 and vertebra V2 at the surgical site. The cutter is manipulated to disrupt and/or remove tissue to form a cavity in vertebral space S, as shown in FIG. 13. In some embodiments, implant strategy 420 may include surgical parameters for creating a surgical pathway for discectomy and channel 84 can be employed to facilitate delivery of the cutter to vertebral space S and discectomy, similar to that described with regard to surgery 700.

Figure 13A:
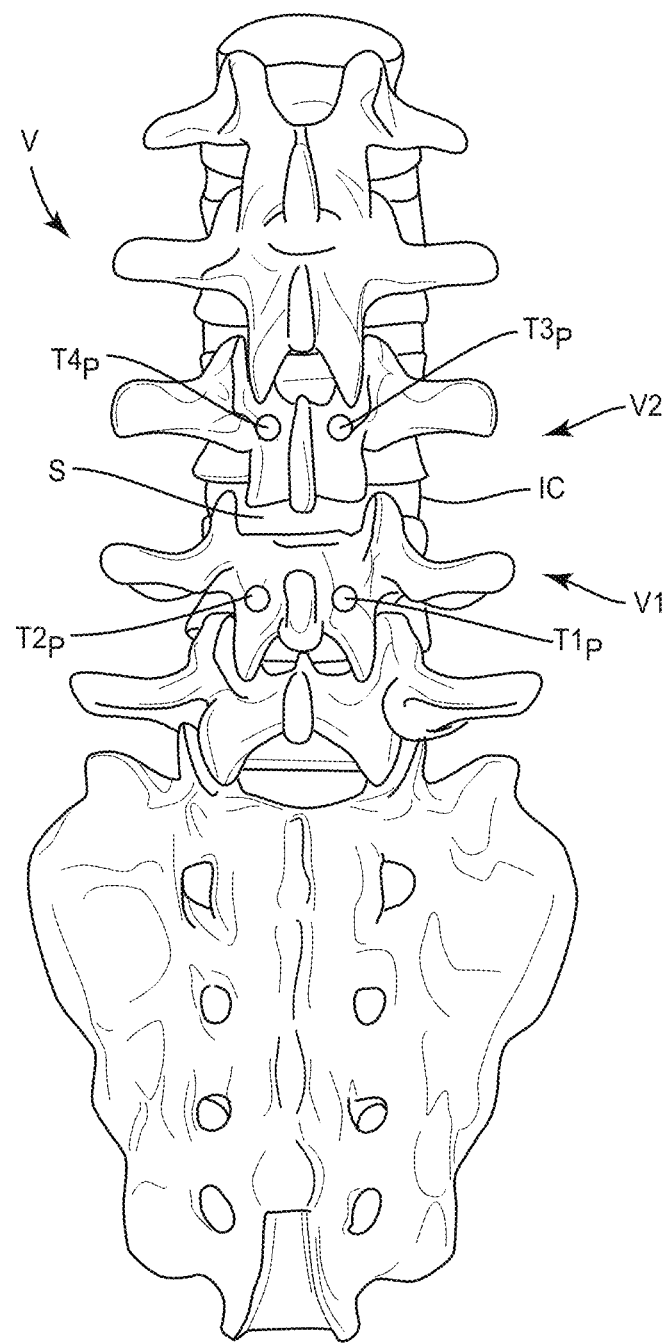
FIG. 13A is a plan view of one embodiment of an implant strategy with vertebrae in accordance with the principles of the present disclosure.

In some embodiments, manipulation step 770 can include a step 820, which includes interbody devices (not shown) being implanted with vertebral space S for selected treatment in connection with a surgical procedure, as described herein. In one embodiment, as shown in FIG. 13A, an inserter (not shown) is connected with an interbody cage IC for disposal with vertebral space S. Subsequent to manipulation step 770, screw shafts 22 are disposed in a modified, adjusted, different or the same position, orientation and/or location with vertebrae V along corresponding post-manipulation screw trajectories T1p, T2p, T3p, T4p, relative to pre-manipulation trajectories T1, T2, T3, T4. In some embodiments, implant strategy 420 may include surgical parameters for creating a surgical pathway for implant of an interbody device and channel 84 can be employed to facilitate delivery of the interbody device to vertebral space S for implant, similar to that described with regard to surgery 700.

In one embodiment, as shown in FIG. 10B, in a surgical step 870, subsequent to manipulation step 770, the three-dimensional position data points of screw shaft 22 disposed along post-manipulation screw trajectory T1p are acquired to identify the post-manipulation position, orientation and/or location of screw shaft 22 relative to vertebra V1. In some embodiments, driver 18 is connected with screw shaft 22 to generate a signal, similar to that described herein, representative of a three-dimensional position, orientation and/or location of screw shaft 22 relative to vertebra V1. Navigation component 58 of driver 18 generates a signal representative of post-manipulation position, orientation and/or location data points of screw shaft 22 relative to driver 18 and/or vertebra V1, similar to that described herein. In some embodiments, medical imaging, as described herein, is employed to identify and generate data points of the post-manipulation position, orientation and/or location of screw shaft 22 relative to vertebra V1. In some embodiments, step 870 includes acquiring the three-dimensional position data points of screw shafts 22 disposed along screw trajectories T2p, T3p, T4p to identify the post-manipulation position, orientation and/or location of the particular screw shaft 22 relative to vertebra V1, V2, similar to screw shaft 22 disposed along screw trajectory T1p.

In a step 875, navigation component 58 transmits the signal and communicates with a processor of computer 64 of surgical navigation system 16, similar to that described herein, which digitally acquires the post-manipulation data points of screw trajectory T1p and/or position, orientation and/or location of screw shaft 22 fixed with vertebra V1 to generate data for display of an image of screw shaft 22 fixed with vertebra V1 on a monitor 66, as described herein. See, for example, similar surgical navigation components and their use as described in U.S. Pat. Nos. 6,021,343, 6,725, 080, 6,796,988, the entire contents of each of these references being incorporated by reference herein. In some embodiments, surgical robotic guidance system 12 and/or surgical navigation system 16 digitally acquire the post-manipulation data points of screw trajectory T1p and/or position, orientation and/or location of screw shaft 22 fixed with vertebra V1 from medical imaging, as described herein, which is transmitted to a corresponding computer database for storage. In some embodiments, surgical robotic guidance system 12 and/or surgical navigation system 16 determines and/or the acquired data points can include post-manipulation position, orientation and/or location of screw shaft 22 relative to vertebra V1, for example, screw shaft 22 penetration depth with vertebra V1 for attaching receiver 28 with screw shaft 22.

For example, in step 875, the acquired post-manipulation data points of screw shaft 22 relative to vertebra V1 are transmitted to computer 64 where they may be forwarded to a computer 76, and may be saved with a database for retrieval during surgery, as described herein with regard to a surgical step 880. In some embodiments, the acquired post-manipulation data points of screw shaft 22 relative to vertebra V1 can be displayed via monitor 66, and digitally manipulated, or printed. In some embodiments, images may also be displayed to the surgeon through a heads-up display. In some embodiments, surgical navigation system 16 provides for real-time tracking, as described herein, of the position of screw shaft 22 relative to vertebra V1. In some embodiments, the position sensors are mounted with robotic arm 14 and calibrated to measure positional data points of end effector 20 in three dimensional space, which are communicated to the components of surgical robotic guidance system 12 and/or computer 64. See, for example, the surgical robotic guidance systems and methods described in U.S. Pat. No. 8,571,638, the contents of which being hereby incorporated by reference herein in its entirety. In some embodiments, step 875 includes transmitting the acquired data points of screw shafts 22 disposed along screw trajectories T2p, T3p, T4p to computer 64 where they may be forwarded to a computer 76, and may be saved with a database for retrieval during surgery, similar to screw shaft 22 disposed along screw trajectory T1p.

In some embodiments, surgical navigation system 16 registers the acquired data points of screw shaft 22 relative to vertebra V1, pre or post-manipulation, as described herein, relative to patient anatomy and/or a three dimensional working space of robot 86, similar to that described herein, and may include a reference marker visible by surgical navigation system 16. This configuration of spinal implant system 10, in combination with imaging of the patient anatomy, is saved with a database of surgical robotic guidance system 12 and/or surgical navigation system 16 and enables registering the acquired data points of screw shaft 22 relative to vertebra V1 and/or three dimensional working space of robot 86. In some embodiments, surgical step 860 and/or surgical step 870 includes a calibration step and/or surgical plan registration for attaching receiver 28 with screw shaft 22 employing medical imaging, similar to that described herein.

Figure 5:
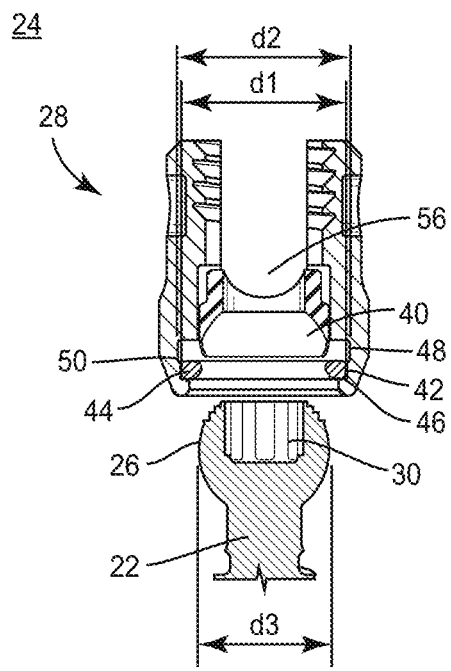
FIG. 5 is a side, cross section view of components of one embodiment of a surgical system in accordance with the principles of the present disclosure.
Figure 6:
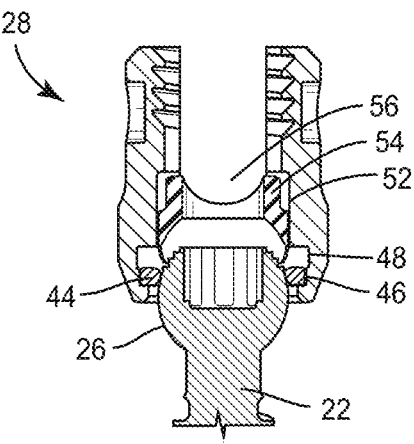
FIG. 6 is a side view of the components shown in FIG. 5.
Figure 7:
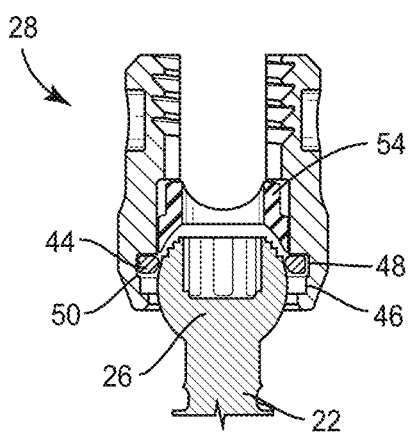
FIG. 7 is a side view of the components shown in FIG. 5.
Figure 8:
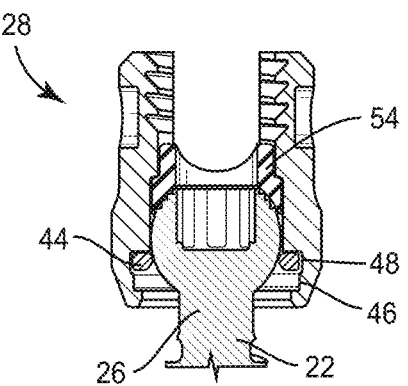
FIG. 8 is a side view of the components shown in FIG. 5.

In some embodiments, during surgery 700, in a step 780, a receiver 28 is selected and manipulated, via instrumented assembly as described herein, for attachment with each screw shaft 22 to form bone fastener 24 having a selected movement, as described herein. Receiver 28 includes ring 44 disposed in channel 46 in a contracted and/or capture orientation having a diameter d1, as shown in FIG. 5. In some embodiments, receiver 28 is manually engaged with head 26, as shown in FIG. 6, such that ring 44 translates from channel 46 into channel 48 over lip 50, as shown in FIG. 7. As head 26 engages ring 44, ring 44 expands to an expanded orientation, as shown in FIG. 7, and head 26 passes through ring 44. In the expanded orientation, ring 44 expands to diameter d2 (FIG. 5) in channel 48. Diameter d3 of head 26 passes through ring 44, as shown in FIG. 8, and the resiliency of ring 44 causes ring 44 to contract and translate along the surface of head 26. As ring 44 contracts back to the capture orientation, ring 44 translates over lip 50 into channel 46, as shown in FIG. 9. Diameter d3 of head 26 prevents head 26 from moving through ring 44 when ring 44 returns to channel 46. In some embodiments, implant strategy 420 may include surgical parameters for delivery and attachment of receiver 28 employing surgical robotic guidance system 12 and/or surgical navigation system 16.

In one embodiment, as shown in FIG. 10B, during surgery 700, in a surgical step 880, the acquired post-manipulation data points of screw shaft 22 relative to vertebra V1 along screw trajectory T1p are retrieved from the computer database of surgical robotic guidance system 12 and/or surgical navigation system 16, as described with regard to surgical steps 870, 875, for attaching receiver 28 with screw shaft 22, similar to surgical step 780. In some embodiments, the acquired data points of screw shafts 22 relative to vertebral tissue along trajectories T2p, T3p, T4p are retrieved from the computer database of surgical robotic guidance system 12 and/or surgical navigation system 16 for attaching receivers 28 with screw shafts 22, similar to surgical step 780. In some embodiments, the acquired data points are retrieved and transmitted to surgical robotic guidance system 12, similar to that described herein, such that robot 86 can move arm 14 and/or align channel 84 with a selected trajectory, location or orientation. In some embodiments, the acquired data points are retrieved and transmitted to control unit 87 to move arm 14 and/or align channel 84, which may include use of a mouse, joystick, touch screen, or the like; and monitor 66. In some embodiments, the acquired pre-manipulation data points of screw shafts 22 relative to vertebral tissue along trajectories T1, T2, T3, T4, as described with regard to steps 860, 865, are retrieved from the computer database of surgical robotic guidance system 12 and/or surgical navigation system 16 for attaching receivers 28 with screw shafts 22, similar to surgical step 780.

In one embodiment, during surgical step 880, the acquired post-manipulation data points of screw shafts 22 relative to vertebra V1, V2 along screw trajectories T1*p*, T2*p*, T3*p*, T4*p* are retrieved and in a step 890, a receiver 28 is selected and disposed with channel 84. The selected receivers 28 are connected and/or captured with arm 14. Arm 14 is moved to align channel 84 with a surgical pathway along screw trajectories T1*p*, T2*p*, T3*p*, T4*p* to each screw shaft 22. Arm 14 manipulates the selected receiver 28 based on the acquired post-manipulation data points for attachment with each screw shaft 22 to form bone fastener 24 having a selected movement, as described herein. The surgeon attaches the selected receiver 28 with each screw shaft 22 via instrumented assembly as described herein. In some embodiments, the retrieved data points include and/or the software of surgical robotic guidance system 12 and/or surgical navigation system 16 determines and provides coupling parameters for attaching the selected receiver 28 with head 26. For example, the coupling parameters may include an attachment of receiver 28 with head 26 such as snap-fit, pop-on and/or coupling at a selected force, pull-off force or separation force, as described herein.

In some embodiments, the software of surgical robotic guidance system 12 and/or surgical navigation system 16 retrieves screw-receiver geometry from the database in step 880. Tracking system 72 tracks placement of receiver 28 relative to a center location of head 26 and may include implant strategy 420 based on receiver 28 size and configuration relative to vertebrae V to avoid interference or injury with patient anatomy. In some embodiments, this configuration of spinal implant system 10 overcomes visibility obstruction and/or visibility challenges associated with screw shank location. In some embodiments, the software of surgical robotic guidance system 12 and/or surgical navigation system 16 provide confirmation of alignment of receiver 28 with head 26 via visual indicia, for example, monitor 66 or heads up display showing a colored (for example, green) check mark, colored border or prompt screen.

In some embodiments, during surgery 700, a step 790 includes attaching spinal rods (not shown) with vertebrae V. A rod inserter (not shown) is connected with a spinal rod. The spinal rod is positioned along vertebrae V and disposed with cavities 56 of receivers 28 attached with screw shafts 22 fastened with a lateral side of vertebra V1 and vertebra V2. A second spinal rod is similarly disposed with cavities 56 of receivers 28 attached with screw shafts 22 fastened with a contra-lateral side of vertebra V1 and vertebra V2. A rod reducer (not shown) is translated into alignment with the surgical site. The spinal rods are reduced into cavities 56. Set screws (not shown) are delivered into engagement with receivers 28. A driver (not shown) is actuated to engage the set screws with receivers 28 to fix the spinal rods with vertebrae V.

Figure 17:
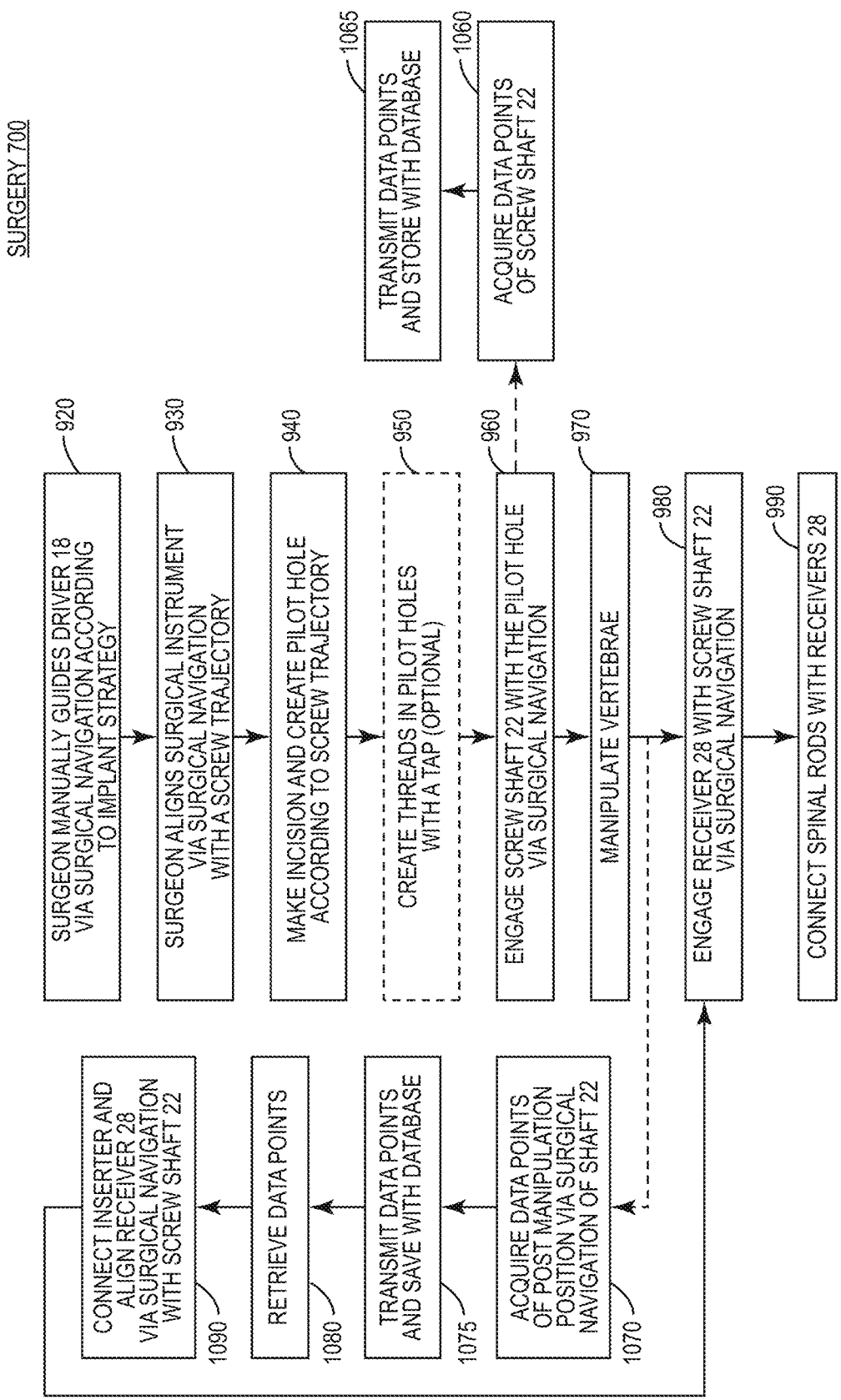
FIG. 17 is a flow diagram illustrating representative steps of embodiments of a method and a surgical system in accordance with the principles of the present disclosure.

In one embodiment, as shown in FIG. 17, spinal implant system 10 employs surgical navigation system 16, without the use of surgical robotic guidance system 12, in connection with surgery 700, similar to that described herein, to register imaging of patient anatomy with imaging of a surgical instrument, place screw shaft 22 with vertebrae V, acquire data points representative of a position of screw shaft 22 relative to vertebrae V, prior and subsequent to manipulation of vertebrae V, as described herein, transmit and store the data points with a computer database of surgical navigation system 16, and retrieve the data points from the computer database for attaching receiver 28 with screw shaft 22, as described herein.

The components of spinal implant system 10 are employed with a method for treating a spine that includes a preparation and/or a pre-operative step, similar to step 400, as described herein with regard to FIG. 10A. The procedure includes a calibration imaging step, similar to step 500, which includes making an incision in the patient at a site where a patient reference frame (not shown), for example, a pin or clamp, is attached to a selected portion of the patient anatomy, such as, for example, vertebra. The reference frame is attached with a pelvis, sacrum or ilium of the patient and includes an emitter or reflector array to communicate a signal to sensor array 60. For example, surgical navigation system 16 registers the patient anatomy, similar to that described herein, relative to the location of the reference frame, such that a surgical instrument can be employed to assist in surgical procedures. The patient anatomy and the surgical instrument may each have reference markers, similar to those described herein, which are visible by surgical navigation system 16. This, in combination with imaging of the patient anatomy, as described herein and stored with surgical navigation system 16, enables registering the patient's anatomy with respect to the reference frame and a surgical instrument. In some embodiments, the imaging includes taking C-arm images of the patient anatomy and these images are calibrated such that a three-dimensional image of the selected vertebra is generated, similar to that described herein.

During registration, similar to step 600, the three-dimensional scans from a preparation step and medical imaging from calibration are transferred to computers 64, 76. As such, sensor array 60 receives signals from emitter array 62 to provide a three-dimensional spatial position and/or a trajectory of screw shaft 22 relative to a surgical instrument and/or vertebrae V, as described herein. One or more surgical instruments can be manipulated by the surgeon adjacent to selected vertebra in a three-dimensional image according to an implant strategy, for example, implant strategy 420 described herein for insertion of surgical tools, medical devices, or implants with a surgical site.

During surgery 700, as shown in FIG. 17, a surgeon manually controls a surgical instrument, for example, driver 18 via surgical navigation system 16, in a step 920, to guide implants, as described herein, at a trajectory and position according to a selected implant strategy. The surgeon moves driver 18 into position as facilitated by surgical navigation system 16, such that a spinal construct component and/or surgical instrument can be aligned with a location according to the implant strategy.

For example, the selected implant strategy can include screw trajectory T1, described herein, of an insertion path and positioning of screw shaft 22 with vertebra V1, as shown in FIG. 13. During surgery 700, in a step 930, the surgeon moves one or more surgical instruments, as described herein, into alignment with screw trajectory T1 as facilitated by surgical navigation system 16. Surgical navigation system 16 generates data for display of a three-dimensional image, spatial position and/or a trajectory of screw shaft 22 relative to one or more surgical instruments and/or vertebrae V, as described herein, on monitor 66. In some embodiments, one or more of the surgical instruments, for example, cutting instrument, drill and/or tap instrument may include a navigation component, similar to navigation component 58 described herein, to generate display from monitor 66. In some embodiments, a sleeve, cannula and/or dilator is disposed with the patient anatomy to define a surgical pathway along a screw trajectory, for example, screw trajectory T1 to vertebra V1.

In a step 940, the surgeon positions a cutting instrument (not shown) within a surgical pathway corresponding to screw trajectory T1. The cutting instrument is translated by the surgeon in alignment with screw trajectory T1 and creates an incision to define a surgical pathway through tissue to vertebra V1. The surgeon removes the cutting instrument from the surgical pathway and the surgeon positions a drill (not shown) within the surgical pathway. The drill is translated by the surgeon in alignment with screw trajectory T1 via surgical navigation. The drill is actuated to create a pilot hole in vertebra V1 along screw trajectory T1. The drill is removed from the surgical pathway.

In some embodiments, in a step 950, the surgeon positions a tap instrument, similar to tap instrument 200 described herein, within the surgical pathway via surgical navigation. The tap instrument forms threads in vertebral tissue about the pilot hole to facilitate fixation and positioning of screw shaft 22 with vertebra V1 along screw trajectory T1. The tap instrument is actuated to create threads in vertebral tissue about the pilot hole and removed from the surgical pathway. In a surgical step 960, prior to manipulation of vertebrae V, for example, decompression, disc preparation and/or interbody insertion, screw shafts 22 are engaged with vertebrae V. Screw shaft 22 is connected with driver 18, as described herein, and the surgeon positions driver 18 with screw shaft 22 extending therefrom within the surgical pathway. Driver 18 is translated by the surgeon through the surgical pathway in alignment with screw trajectory T1 via surgical navigation. Screw shaft 22 engages vertebra V1 and driver 18 is manipulated to drive, torque, insert or otherwise connect screw shaft 22 with the pilot hole of vertebra V1 along screw trajectory T1 according to the implant strategy, as shown in FIG. 15. Driver 18 is disengaged from screw shaft 22, as described herein and shown in FIG. 16. In some embodiments, step 960 includes engaging screw shafts 22 with vertebrae V disposed along screw trajectories T2, T3, T4, similar to screw shaft 22 disposed along screw trajectory T1.

During surgery 700, as shown in FIG. 17, screw shaft 22 is fixed with vertebra V1 along screw trajectory T1 and in a surgical step 1060, navigation component 58 of driver 18 generates a signal to facilitate acquisition of data points of the three-dimensional position of screw shaft 22 relative to vertebra V1, similar to that described herein. In some embodiments, step 1060 includes navigation component 58 generating a signal representative of a position of respective screw shafts 22 along screw trajectories T2, T3, T4 relative to driver 18 to facilitate acquisition of data points of the three-dimensional position of screw shafts 22 relative to vertebrae V, similar to that described herein.

In a step 1065, navigation component 58 transmits the signal and communicates with a processor of computer 64 of navigation system 16, similar to that described herein, which digitally acquires the data points of screw trajectory T1 and/or position, orientation and/or location of screw shaft 22 fixed with vertebra V1 to generate data for display of an image of screw shaft 22 fixed with vertebra V1 on monitor 66, similar to that described herein. Surgical navigation system 16 digitally acquires data points of screw trajectory T1 and/or position, orientation and/or location of screw shaft 22 fixed with vertebra V1 from medical imaging, as described herein, which is transmitted to a corresponding computer database for storage. The acquired data points of screw shaft 22 relative to vertebra V1 are transmitted to computer 64 where they may be forwarded to a computer 76, and may be saved with a database for retrieval during surgery, similar to that described herein and with regard to surgical step 1080. In some embodiments, surgical navigation system 16 registers the acquired data points of screw shaft 22 relative to vertebra V1 and/or relative to patient anatomy. This configuration of spinal implant system 10, in combination with imaging of the patient anatomy, is saved with a database of surgical navigation system 16 and enables registering the acquired data points of screw shaft 22 relative to vertebra V1. In some embodiments, step 1065 includes transmitting the acquired data points of screw shafts 22 disposed along screw trajectories T2, T3, T4 to computer 64 where they may be forwarded to a computer 76, and may be saved with a database for retrieval during surgery, similar to screw shaft 22 along screw trajectory T1.

With one or more screw shafts 22 engaged with vertebrae V, as described during surgery 700, vertebrae V is subsequently manipulated in a step 970 for selected treatment in connection with a surgical procedure, similar to that described herein. In some embodiments, subsequent to manipulation step 970, screw shafts 22 are disposed in a modified, adjusted, different or the same position, orientation and/or location with vertebrae V along corresponding post-manipulation screw trajectories T1p, T2p, T3p, T4p, similar to that described herein.

In a surgical step 1070, as shown in FIG. 17, subsequent to manipulation step 970, the three-dimensional position data points of screw shaft 22 disposed along post-manipulation screw trajectory T1p are acquired via surgical navigation to identify the post-manipulation position, orientation and/or location of screw shaft 22 relative to vertebra V1. Driver 18 is connected with screw shaft 22 to generate a signal representative of a three-dimensional position, orientation and/or location of screw shaft 22 relative to vertebra V1. Navigation component 58 of driver 18 generates a signal representative of post-manipulation position, orientation and/or location data points of screw shaft 22 relative to driver 18 and/or vertebra V1. Medical imaging is employed to identify and generate data points of the post-manipulation position, orientation and/or location of screw shaft 22 relative to vertebra V1. In some embodiments, step 1070 includes acquiring the three-dimensional position data points of screw shafts 22 disposed along screw trajectories T2p, T3p, T4p to identify the post-manipulation position, orientation and/or location of the particular screw shaft 22 relative to vertebra V1, V2, similar to screw shaft 22 along screw trajectory T1p.

In a step 1075, navigation component 58 transmits the signal and communicates with a processor of computer 64 of surgical navigation system 16, similar to that described herein, which digitally acquires the post-manipulation data points of screw trajectory T1p and/or position, orientation and/or location of screw shaft 22 fixed with vertebra V1 to generate data for display of an image of screw shaft 22 fixed with vertebra V1 on a monitor 66. Surgical navigation system 16 digitally acquires the post-manipulation data points of screw trajectory T1p and/or position, orientation and/or location of screw shaft 22 fixed with vertebra V1 from medical imaging, which is transmitted to a corresponding computer database for storage. Surgical navigation system 16 determines and/or the acquired data points can include post-manipulation position, orientation and/or location of screw shaft 22 relative to vertebra V1, for example, screw shaft 22 penetration depth with vertebra V1 for attaching receiver 28 with screw shaft 22.

For example, in step 1075, the acquired post-manipulation data points of screw shaft 22 relative to vertebra V1 are transmitted to computer 64 where they may be forwarded to a computer 76, and may be saved with a database for retrieval during surgery, as described herein with regard to a surgical step 1080. Surgical navigation system 16 displays the acquired post-manipulation data points of screw shaft 22 relative to vertebra V1 from monitor 66. Surgical navigation system 16 provides for real-time tracking, as described herein, of the position of screw shaft 22 relative to vertebra V1. In some embodiments, step 1075 includes transmitting the acquired data points of screw shafts 22 disposed along screw trajectories T2p, T3p, T4p to computer 64 where they may be forwarded to a computer 76, and may be saved with a database for retrieval during surgery, similar to screw shaft 22 disposed along screw trajectory T1p.

In some embodiments, surgical navigation system 16 registers the acquired data points of screw shaft 22 relative to vertebra V1, pre or post-manipulation as described herein, relative to patient anatomy, similar to that described herein, and may include a reference marker visible by surgical navigation system 16. This configuration of spinal implant system 10, in combination with imaging of the patient anatomy, is saved with a database of surgical navigation system 16 and enables registering, similar to that described herein, the acquired data points of screw shaft 22 relative to vertebra V1. In some embodiments, surgical step 1060 and/or surgical step 1070 includes a calibration step and/or surgical plan registration for attaching receiver 28 with screw shaft 22 employing medical imaging, similar to that described herein.

In a surgical step 1080, the acquired post-manipulation data points of screw shaft 22 relative to vertebra V1 along screw trajectory T1p are retrieved from the computer database of surgical navigation system 16, as described with regard to surgical steps 1070, 1075, for attaching a selected receiver 28 with screw shaft 22 in a step 980, similar to that described herein. In some embodiments, the acquired data points of screw shafts 22 relative to vertebral tissue along trajectories T2p, T3p, T4p are retrieved from the computer database of surgical navigation system 16 for attaching selected receivers 28 with screw shafts 22. In some embodiments, the acquired pre-manipulation data points of screw shafts 22 relative to vertebral tissue along trajectories T1, T2, T3, T4, as described with regard to steps 1060, 1065, are retrieved from the computer database of surgical navigation system 16 for attaching receivers 28 with screw shafts 22.

In one embodiment, during surgical step 1080, the acquired post-manipulation data points of screw shafts 22 relative to vertebra V1, V2 along screw trajectories T1p, T2p, T3p, T4p are retrieved and in a step 1090, a receiver 28 is selected for manual and/or instrumented connection with each screw shaft 22. The selected receiver 28 is connected and/or captured with an inserter (not shown) manipulated by the surgeon. The inserter includes a navigation component, similar to navigation component 58, to generate display from monitor 66, similar to that described herein. The inserter is moved to align receiver 28 with a surgical pathway along screw trajectories T1p, T2p, T3p, T4p to each screw shaft 22 via surgical navigation and real time tracking, as described herein. In a step 980, the surgeon manipulates the selected receiver 28 via surgical navigation based on the acquired post-manipulation data points for attachment with each screw shaft 22 to form bone fastener 24 having a selected movement, as described herein. The surgeon attaches the selected receiver 28 with each screw shaft 22 via manual and/or instrumented assembly, similar to that described herein.

In some embodiments, the software of surgical navigation system 16 retrieves screw-receiver geometry from the database in step 1080. Tracking system 72 tracks placement of receiver 28 relative to a center location of head 26 and may include an implant strategy based on receiver 28 size and configuration relative to vertebrae V to avoid interference or injury with patient anatomy. In some embodiments, the software of surgical navigation system 16 provides confirmation of alignment of receiver 28 with head 26 via visual indicia, for example, monitor 66 or heads up display showing a colored (for example, green) check mark, colored border or prompt screen. In some embodiments, during surgery 700, a step 990 includes attaching one or more spinal rods (not shown) with vertebrae V, similar to step 790.

Upon completion of one or more surgical procedures, the surgical instruments and non-implanted components of spinal implant system 10 are removed and the incision(s) are closed. One or more of the components of spinal implant system 10 can be made of radiolucent materials such as polymers. In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating a spine, the method comprising the steps of:
   imaging a patient anatomy including a vertebra;
   selecting an implant strategy according to the imaging for a screw shaft;
   generating fluoroscopic images of at least a portion of a robot;
   registering the imaging of the patient anatomy with the fluoroscopic images;
   engaging the screw shaft with the vertebra via the surgical driver according to the implant strategy;
   acquiring a first set of data points representative of a three dimensional position of the screw shaft relative to the vertebra;
   transmitting the first set of data points to a computer database;
   manipulating the patient anatomy;
   acquiring a second set of data points representative of a three dimensional position of the screw shaft relative to the vertebra subsequent to manipulating the patient anatomy;
   transmitting the second set of data points to the computer database;

retrieving the second set of data points from the computer database;
aligning an implant receiver with the screw shaft according to the second set of data points; and
engaging the implant receiver with the screw shaft to comprise a bone screw.

2. A method as recited in claim 1, wherein the step of acquiring the first set of data points includes a navigation component of the surgical driver generating a signal representative of a position of the screw shaft relative to the surgical driver.

3. A method as recited in claim 1, wherein the surgical driver is connected with a surgical robot and the step of acquiring the first set of data points includes a navigation component of the surgical driver generating a signal representative of a position of the screw shaft relative to the surgical driver.

4. A method as recited in claim 3, wherein the surgical robot includes position sensors and the step of acquiring the first set of data points includes the position sensors generating a signal representative of a position of the screw shaft relative to the surgical driver.

5. A method as recited in claim 1, wherein the step of acquiring the first set of data points includes data points comprising a three-dimensional position of the screw shaft relative to the vertebra.

6. A method as recited in claim 1, wherein the screw shaft has a head and the step of acquiring the first set of data points includes data points comprising a three-dimensional position of the head relative to the patient anatomy.

7. A method as recited in claim 1, wherein the screw shaft has a head and the step of acquiring the first set of data points includes data points comprising a position of a center of the head relative to the patient anatomy.

8. A method as recited in claim 1, wherein the step of acquiring the first set of data points includes data points representative of penetration depth of the screw shaft with the patient anatomy.

9. A method as recited in claim 1, wherein the step of acquiring the first set of data points includes data points generated from a CT scan.

10. A method as recited in claim 1, further comprising the step of displaying the first set of data points from a computer monitor.

11. A method as recited in claim 1, wherein engaging the implant receiver with the screw shaft includes inserting a head of the screw shaft into a cavity of the implant receiver.

12. A method as recited in claim 11, further comprising the step of tracking placement of the implant receiver with the screw shaft.

13. A method as recited in claim 11, further comprising the step of displaying indicia of confirmation of alignment of the implant receiver with the screw shaft.

14. A method as recited in claim 1, wherein engaging the implant receiver with the screw shaft comprises manually engaging the implant receiver with the screw shaft to connect the members.

15. A method as recited in claim 14, wherein the step of manually engaging the members includes snap fitting the screw shaft with the implant receiver.

16. A method as recited in claim 1, wherein the step of imaging a patient anatomy includes pre-operatively generating three dimensional images of the patient anatomy.

17. A method as recited in claim 1, wherein the step of selecting the implant strategy includes pre-operative planning according to the imaging of the patient anatomy.

18. A method as recited in claim 1, wherein the screw shaft includes a plurality of screw shafts and the implant strategy includes a plurality of screw trajectories for positioning the screw shafts with the vertebra and a second vertebra of the patient anatomy.

19. A method for treating a spine, the method comprising the steps of:
pre-operatively generating a CT scan of a patient anatomy including at least one vertebra;
selecting an implant strategy according to the CT scan for at least one bone screw shaft;
generating fluoroscopic images of at least a portion of a robot;
registering the CT scan with the fluoroscopic images;
engaging the bone screw shaft with the vertebra via robotic guidance according to the implant strategy;
acquiring a first set of data points representative of a three dimensional position of the at least one bone screw shaft relative to the at least one vertebra;
transmitting the first set of data points to a computer database;
subsequently, manipulating the patient anatomy;
acquiring a second set of data points representative of a three dimensional position of the at least one bone screw shaft relative to the at least one vertebra subsequent to manipulating the patient anatomy;
transmitting the second set of data points to the computer database;
retrieving the second set of data points from the computer database;
aligning an implant receiver with the bone screw shaft according to the second set of data points; and
manually engaging the implant receiver with the bone screw shaft to comprise a bone screw.

20. A method for treating a spine, the method comprising the steps of:
imaging vertebral tissue;
selecting an implant strategy for at least one bone screw shaft;
registering the imaging of the vertebral tissue with imaging of a robot connected with the vertebral tissue;
connecting a surgical driver with the bone screw shaft, the surgical driver including an image guide oriented relative to a sensor to communicate a signal representative of a three dimensional position of the bone screw shaft relative to the vertebral tissue;
engaging the bone screw shaft with the vertebral tissue via robotic guidance according to the implant strategy;
acquiring a first set of data points representative of the three dimensional position of the at least one bone screw shaft according to the signal;
transmitting the first set of data points to a computer database;
subsequently, manipulating the vertebral tissue;
acquiring a second set of data points representative of a three dimensional position of the bone screw shaft relative to the vertebral tissue subsequent to manipulating the vertebral tissue;
transmitting the second set of data points to the computer database;
retrieving the second set of data points from the computer database;
aligning an implant receiver with the bone screw shaft according to the second set of data points; and manually engaging the implant receiver with the bone screw shaft to comprise a bone screw.

\* \* \* \* \*